(12) United States Patent
Carothers et al.

(10) Patent No.: US 12,070,579 B2
(45) Date of Patent: *Aug. 27, 2024

(54) OCCLUSION DETECTION FOR INFUSION PUMPS

(71) Applicant: CareFusion 303, Inc., San Diego, CA (US)

(72) Inventors: Kevin Gregory Carothers, San Diego, CA (US); Richard Stor Wu, San Diego, CA (US); Robert Dwaine Butterfield, Poway, CA (US); Robert Steven Vasko, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/230,900

(22) Filed: Aug. 7, 2023

(65) Prior Publication Data

US 2023/0381410 A1 Nov. 30, 2023

Related U.S. Application Data

(63) Continuation of application No. 17/013,421, filed on Sep. 4, 2020, now Pat. No. 11,771,825, which is a
(Continued)

(51) Int. Cl.
*A61M 5/168* (2006.01)
*G01L 7/04* (2006.01)
(Continued)

(52) U.S. Cl.
CPC .......... *A61M 5/16859* (2013.01); *G01L 7/04* (2013.01); *G06N 5/04* (2013.01); *G06N 20/00* (2019.01);
(Continued)

(58) Field of Classification Search
None
See application file for complete search history.

(56) References Cited

U.S. PATENT DOCUMENTS

| 4,882,575 A | 11/1989 | Kawahara |
| 5,103,211 A | 4/1992 | Daoud et al. |
| (Continued) | | |

FOREIGN PATENT DOCUMENTS

CN 105706089 A 6/2016

OTHER PUBLICATIONS

Australian Office Action for Application No. 2018354262, dated Oct. 24, 2023, 4 pages.
European Office Action for Application No. 18801156.3, dated Oct. 24, 2023, 5 pages.
Australian Office Action for Application No. 2018354262, dated Jul. 18, 2023, 3 pages.
(Continued)

*Primary Examiner* — Daniel S Larkin
(74) *Attorney, Agent, or Firm* — Morgan, Lewis & Bockius LLP

(57) ABSTRACT

A system including a tube and a force sensor coupled to a wall of the tube via a restraining element and configured to obtain a value of a tubing force when the tube is deformed by the restraining element. The system includes a processor to determine parameters for fitting a curve including the value of the tubing force, to determine a fluid pressure value for a fluid in the tube based on the parameters for fitting the curve, and to activate an alarm responsive to the fluid pressure value and to the parameters for fitting the curve when an occlusion condition is identified in the tube. The parameters for fitting the curve comprise at least one time-decaying parameter(s) associated to the tubing force. A method for using the system and a non-transitory computer readable medium including instructions to perform the above method are also provided.

20 Claims, 16 Drawing Sheets

Related U.S. Application Data continuation of application No. 15/792,226, filed on Oct. 24, 2017, now Pat. No. 10,792,420.

(51) Int. Cl.

| | |
|---|---|
| *G06N 5/04* | (2023.01) |
| *G06N 20/00* | (2019.01) |
| *G08B 21/18* | (2006.01) |
| *G16H 20/17* | (2018.01) |
| *G16H 40/40* | (2018.01) |
| *G16H 40/63* | (2018.01) |
| *G16H 50/50* | (2018.01) |

(52) U.S. Cl.
CPC ........... *G08B 21/182* (2013.01); *G16H 20/17* (2018.01); *G16H 40/40* (2018.01); *G16H 40/63* (2018.01); *A61M 2005/16868* (2013.01); *A61M 2005/16872* (2013.01); *A61M 2205/3553* (2013.01); *A61M 2205/3561* (2013.01); *A61M 2205/3584* (2013.01); *A61M 2205/52* (2013.01); *A61M 2205/583* (2013.01); *G16H 50/50* (2018.01)

(56) References Cited

U.S. PATENT DOCUMENTS

| | | |
|---|---|---|
| 5,695,473 A | 12/1997 | Olsen |
| 5,827,223 A | 10/1998 | Butterfield |
| 6,213,972 B1 | 4/2001 | Butterfield et al. |
| 6,358,225 B1 | 3/2002 | Butterfield |
| 6,648,861 B2 | 11/2003 | Platt et al. |
| 7,255,683 B2 | 8/2007 | Vanderveen et al. |
| 8,182,461 B2 | 5/2012 | Pope et al. |
| 8,378,837 B2 | 2/2013 | Wang et al. |
| 9,039,656 B2 | 5/2015 | Vanderveen et al. |
| 9,839,744 B2 | 12/2017 | Muto et al. |
| 2005/0096593 A1 | 5/2005 | Pope et al. |

OTHER PUBLICATIONS

Canadian Office Action for Application No. 3076019, dated Jan. 24, 2023, 3 pages.
European Office Action for Application No. 18801156.3, dated Mar. 27, 2023, 5 pages.
International Search Report and Written Opinion for Application No. PCT/US2018/057393, dated Jan. 29, 2019, 17 pages.
Chinese Office Action for Application No. 201880069583.X, dated Feb. 29, 2024, 19 pages including translation.

OCCLUSION DETECTION FOR INFUSION PUMPS

CROSS-REFERENCE TO RELATED APPLICATION

This is a continuation of patent application Ser. No. 17/013,421, filed on Sep. 4, 2020, issued as U.S. Pat. No. 11,771,825 on Oct. 3, 2023, entitled "OCCLUSION DETECTION FOR INFUSION PUMPS," which is a continuation of patent application Ser. No. 15/792,226, filed on Oct. 24, 2017, issued as U.S. Pat. No. 10,792,420 on Oct. 6, 2020, entitled "OCCLUSION DETECTION FOR INFUSION PUMPS," the contents of which are hereby incorporated by reference in their entireties for all purposes.

BACKGROUND

The present disclosure is generally related to control mechanisms for infusion pumps in a fluid system. More specifically, the present disclosure relates to devices and methods for detecting and preventing occlusion events for infusion pumps in a healthcare facility.

Infusion control systems available today include mechanisms for pressure measurement that involve invasive sensors in contact with the fluid. These systems, when used for medication infusion devices in healthcare applications, pose the threat of infections and contamination, thereby enhancing protocol costs for using, handling, and disposing of used items. Other systems using non-invasive pressure measurement protocols include sophisticated averaging algorithms and machine learning algorithms to predict when the source of a behavioral change in the infusion process is due to an occlusion. However, the predictability of these algorithms is degraded, especially when certain configuration conditions are changed (e.g., when a different tubing is used, or after pump reconfiguration).

SUMMARY

In one or more embodiments an infusion pump for detection of a fluid condition in a flexible tubing is provided. The infusion pump includes a restraining element for receiving a tube, a sensor coupled to the restraining element and positioned to obtain a value of a tubing force when the tube is engaged by the restraining element, a memory storing instructions and a processor. The processor is configured to execute the instructions to generate a force-time curve representative of values of the tubing force obtained by the sensor over time, determine a time-decaying parameter associated with the tubing force characterizing the force-time curve, determine a fluid pressure value for a fluid in the tube based at least in part on the time-decaying parameter, introduce a pump reversal event and detect that a rate of change of the tubing force exceeds a threshold.

In one more embodiments a method is provided. The method includes generating, with a fluid displacement infusion pump, a fluid flow in a tube; deforming the tube with a restraining element coupled with a wall of the tube; collecting, with a force sensor comprising the restraining element, a value of a tubing force in response to a wall deformation caused by deforming the tube; determining, with a processor, parameters for fitting a curve, the curve comprising values of the tubing force obtained by the force sensor over time, wherein the parameters for fitting the curve comprise at least one time-decaying parameter associated with the tubing force; determining a fluid pressure value for a fluid in the tube based on the parameters for fitting the curve; generating, in the fluid displacement infusion pump, a transient reversal of the fluid flow in the tube; determining a change in the tubing force from a baseline force responsive to the transient reversal; and identifying a blockage condition in the tube based on the change in the tubing force.

BRIEF DESCRIPTION OF THE DRAWINGS

In the figures, elements having the same or similar reference numerals have the same or similar functionality or configuration, unless expressly stated otherwise.

DETAILED DESCRIPTION

Figure 1:
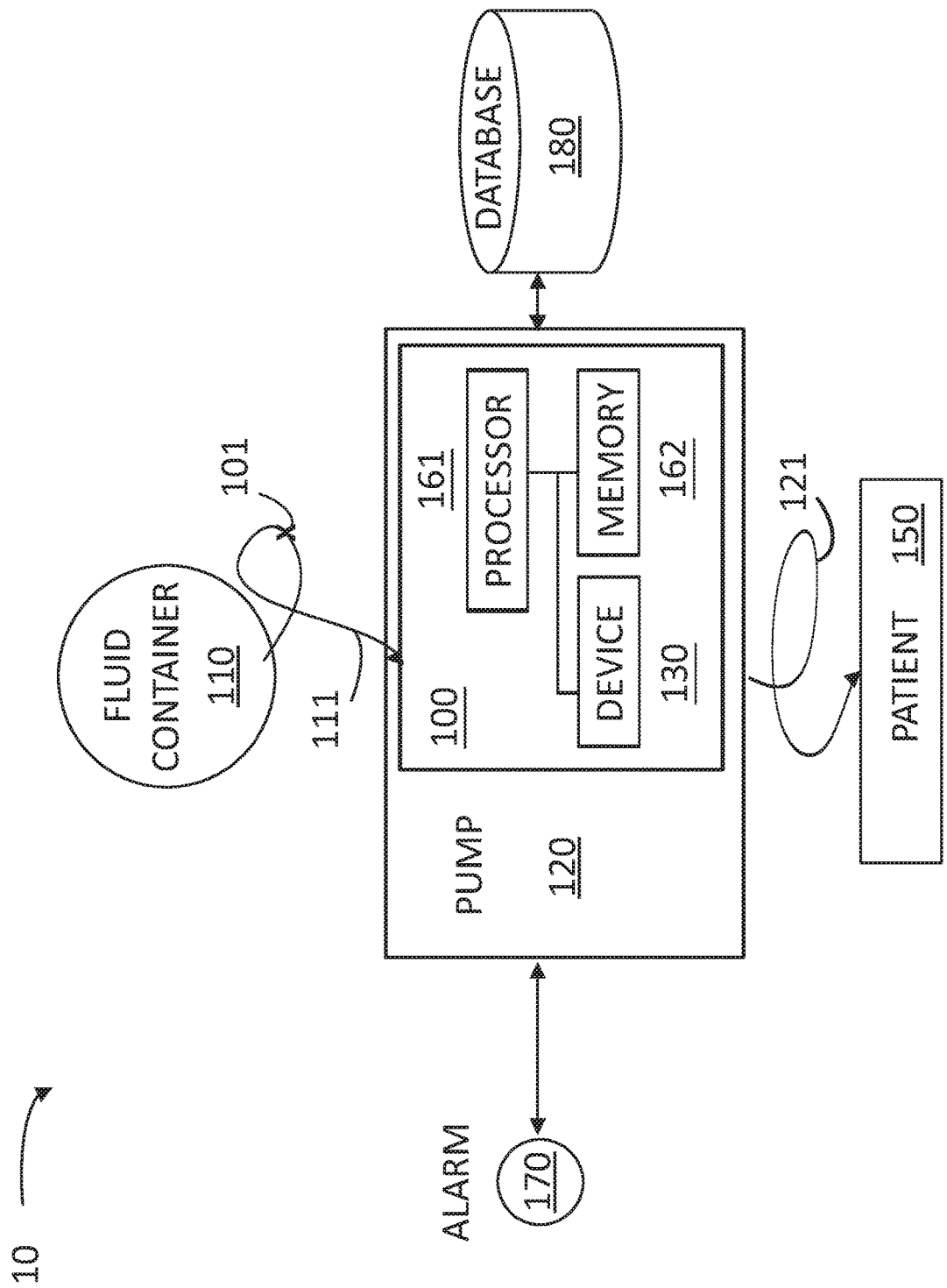
FIG. 1 illustrates an infusion architecture using an occlusion detection system, according to some embodiments.

The disclosure is related to methods and systems for occlusion detection upstream (container-side) and downstream (patient-side) from infusion pumps in medication infusion applications. In a medication infusion system, occlusions may occur along conduits and tubes upstream (e.g., upstream occlusion, or USO) or downstream of a pump that directs the infusion fluid (the "infusate") from a container (e.g., a bag, a bottle, and the like) to the patient. An upstream occlusion may occur when the infusion fluid is unable to reach the pump (and thus to the patient) due to a blockage upstream of the pump. Such blockages may include a closed roller clamp, a blocked filter (e.g., a wetted filter), an inadvertent kink in the tubing, and the like. A downstream occlusion may occur when the infusion fluid is unable to reach the patient due to a blockage downstream of the pump. Such blockages may include a closed roller clamp, an inadvertent kink in the tubing, clotting or blockage of the fluid entry port, and the like. As a result of occlusions and other infusion anomalies, the medication may be under-infused to the patient, potentially creating life threatening emergencies.

Some of the advantages of embodiments consistent with the present disclosure include the use of a regression model that receives measurement from a simple force measurement device and quickly returns coefficients adapted for different types of tubing materials (and behavior) and settings used in medication infusion systems. Measurements as disclosed herein provide accurate and sensitive measurements of a fluid force, thereby reducing the occurrence of false positive and false negative events.

Embodiments as disclosed herein substantially reduce the number of false negative occlusion events by providing accurate modeling of the stress relaxation in the infusion tubing. Accordingly, embodiments as disclosed herein avoid falsely detecting an occlusion event, such as when a tubing has loss resiliency due to misuse or aging or variation due to manufacturing, thereby reducing a total force measured by the system. Further, accurate modeling of data collected by devices and systems as disclosed herein provide a distinction between soft and hard occlusion events. Some embodiments also incorporate data filtering into the modeling to provide assessment of the infusion process that is robust to noise.

Some embodiments include learning the properties of many infusion tubes and from these properties to predict what the wall force component will be at any time. The instantaneous measured force is compared to the model-estimate and a difference is formed. This difference may be used directly or may better be converted to an estimated fluid pressure simply by dividing the present difference by a sensitivity term with units (force per unit pressure). In some embodiments, a method as disclosed herein include performing a medication infusion of a fluid through infusion tubing fluidically coupled with an infusion pump, and performing continuous measurements of the total force (tubing force+fluid force) produced by the infusion tubing when compressed with an external force sensor. The method also includes activating an alarm when the total force is different from the expected force by a pre-determined error value or equivalently when the predicted pressure falls below a user-determined threshold. As time progresses and the wall force reduces due to stress relaxation, the regression model incorporates all prior measured forces to update the estimated tube parameters and thus produce a continually improving prediction of the true wall force over time. When the difference between the current measured force and the predicted force or equivalently the computed pressure exceeds a predetermined threshold, alerts and or alarms are produced. Additionally, the algorithm fits the shape of the curve in sequential windows to determine the local behavior of the signal (e.g., determine the slope of the curve in a specified time window and comparing the slopes of each time window); these values are used to augment the long term based estimates including stress relaxation.

In some embodiments, use of previously stored values or ranges may be used as a check to verify the validity of the fitting algorithm. For example, when an estimate is out of the expected range for many tubes, the algorithm could either 'start over' or reject certain samples.

FIG. 1 illustrates infusion architecture 10 using an occlusion detection system 100, according to some embodiments. Infusion architecture 10 includes a fluid container 110 fluidically coupled with a pump 120 through an upstream conduit or tubing 111. Pump 120 is fluidically coupled with a patient 150 through a downstream conduit or tubing 121, thereby providing the contents of fluid container 110 to patient 150.

An occlusion 101 may occur at any point along either of upstream tubing 111 or downstream tubing 121. Occlusion 101 may be a soft occlusion (e.g., a partial occlusion) or a hard occlusion that may block the fluid flow. A soft upstream occlusion event may be the result of a wetted filter upstream of the infusion line. A hard occlusion event may be caused by a kink in upstream tubing 111 or a closed roller clamp located on the upstream tubing 111. A hard occlusion may include a sudden, complete blockage of the fluid flow.

Occlusion detection system 100 includes a force measurement device 130. Occlusion detection system 100 may also include a processor 161 and a memory 162. In some embodiments, memory 162 stores instructions which, when executed by processor 161, cause occlusion detection system 100 to perform methods as disclosed herein. For example, force measurement device 130 may be configured to provide pressure measurement data to processor 161, which may in turn determine, based on the fluid pressure measurement data, whether occlusion 101 has occurred. Pump 120 may also be communicably coupled with an alarm 170. Accordingly, occlusion detection system 100 may be configured to activate alarm 170 when an occlusion is detected in upstream tubing 111 or in downstream tubing 121. In some embodiments, alarm 170 may include a physical alarm generating a sound and a visual signal. In some embodiments, alarm 170 may include a communication to a centralized server for handling.

In some embodiments, pump 120 may be communicably coupled with a database 180 for retrieving, editing, and/or storing files including historical data of prior occlusion events. Accordingly, in some embodiments memory 162 may include machine learning algorithms, artificial intelligence algorithms, and neural network algorithms trained using historical information stored in database 180. Further in some embodiments, occlusion detection system 100 provides recently collected medication infusion information to database 180 for further training of machine learning algorithms.

Figure 2A:
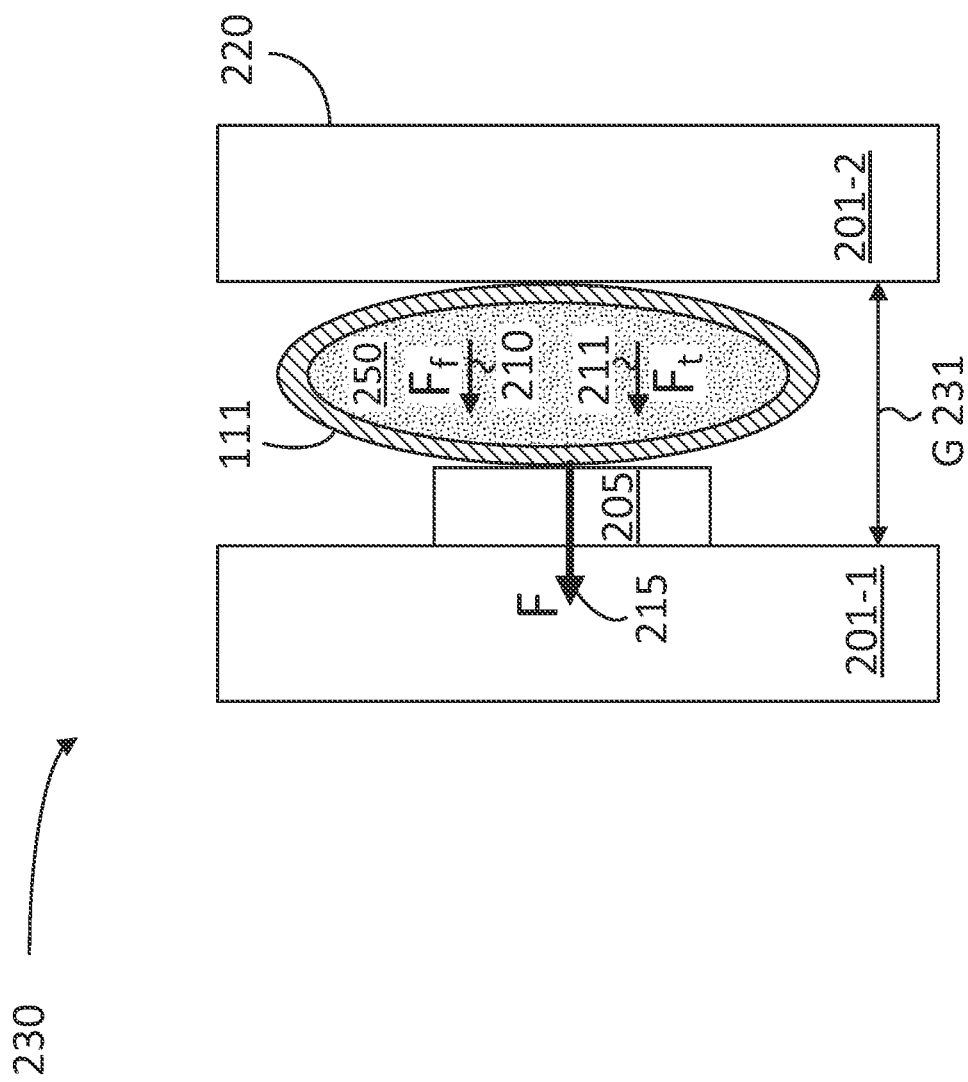
FIG. 2A illustrates a force measurement device to determine a fluid pressure, according to some embodiments.

FIG. 2A illustrates a force measurement device 230, according to some embodiments. Force measurement device 230 includes a vice 220 having a force sensor 205 in one of its compression members or jaws 201-1, and 201-2 (hereinafter, collectively referred to as "jaws 201"). Jaws 201 are configured to squeeze tubing 111 by adjusting a gap G 231 formed therebetween, so as to obtain a slight deformation of the cross section of tubing 111, while pump 120 is in operation. As a result of the deformation, tubing 111 exerts a force 215 (F) against force sensor 205. In general, force F 215 includes two components: a fluid force 210 ($F_f$), and a tube force 211 ($F_t$). $F_t$ 211 is the resilient force that the material for tubing 111 (or tubing 121) exerts against jaws 201 in vice 220 to oppose deformation. $F_f$ 210 is the force exerted against jaws 201 by the pressure of fluid 250 inside tubing 111.

In some embodiments, F 215, $F_f$ 210, and $F_t$ 211 may be related through the following mathematical expression $$F = F_f + F_t. \quad (1)$$

Accordingly, having a precise measure of force F 215, it is desirable to have an accurate model for $F_t$ 211 so that the fluid pressure may be determined from $F_f$. In some embodiments, $F_f$ may be obtained from Eq. 1 as $$F_f = F - F_t = P_{fluid}(r,t) \cdot S \quad (2)$$

wherein $P_{fluid}$ is a fluid pressure (e.g., upstream pump 120) as a function of a pumping rate, r, and time, t, and S is a sensitivity factor that relates the fluid pressure to the tube wall force (e.g., expressed in units of pressure/force and associated with the contact area between tubing 111 and force sensor 205).

In some embodiments, the resiliency of the material in tubing 111 is not constant (e.g., through time, t). Furthermore, the plasticity of the material, which enables deformation of tubing 111 upon a certain stress (e.g., the pressure exerted by jaws 201), implies that, during the time span of a measurement, force $F_t$ 211 is expected to change (e.g., $F_t$ is reduced as tubing 111 complies with a deformation). An accurate model for the function $F_t(t)$ is therefore highly desirable. In some embodiments, it may be assumed that force $F_t$ 211 decays logarithmically in time, following a mathematical expression $$F_t = F(t_o) + m \ln(t). \quad (3)$$

In Eq. 3, '$F(t_o)$' is a constant associated with the initial resilient force at time t=1 (in arbitrary units), and 'm' is the viscoelastic stress relaxation of the material in tubing 111. In some embodiments, m is a negative number, as force $F_t$ is expected to decrease with time (e.g., for a fixed gap G231 in vice 220). The specific values of $F(t_o)$ and m are dependent on the age of tubing 111, on the specific material forming tubing 111 (e.g., silicone and the like), and even on the specific handling of tubing 111. Further, the specific value of $F(t_o)$ may depend on the amount of deformation induced in the tubing by the force measurement device (e.g., G 231). Accordingly, the value of $F(t_o)$ may depend on the exact measurement configuration for tubing 111, and may desirably be re-calibrated using Eq. 3 each time pump 120 is open-closed and restarted. In some embodiments, the initial resilient force, $F(t_o)$, and the creep parameter, m, may be determined using a continuous regression on the tubing force measurements.

In some embodiments, a regression step including Eq. 3 is desirable because parameters $F(t_o)$ and m may be determined with relatively high accuracy within the first few data points after t=1. The behavior of $F_t$ expected may, in fact, remain as modeled by Eq. 3 for long periods of time, involving many cycles of pump 120 after the infusion process has started. Moreover, the regression model in Eq. 3 enables an accurate estimation of the initial tubing resiliency through initial force, $F(t_o)$, which is desirable, as tubing resiliency is a highly varying parameter of infusion architecture 10 (cf. FIG. 1). Moreover, in some embodiments different tubing materials may be used, thereby leading to a substantially different initial force $F(t_o)$ even when G231 is the same. Accordingly, an accurate and fast determination of $F(t_o)$ as provided by Eq. 3 is desirable and advantageous over currently available systems. Another advantage of performing a regression of data points with Eq. 3 is that the regression is linear on the parameters $F(t_o)$ and m, relative to the measurement values, $F_{meas}$.

From Eq. 2, it is seen that when the fluid pressure becomes negative (relative to the atmosphere surrounding vice 220), then $F_f$ is less than zero, and force F 215 drops below an expected value for $F_t$ 211 (cf. Eq. 3). Accordingly, a drop in F 215 below the expected value for $F_t$ in Eq. 3 likely indicates an occlusion event along the line of tubing 111. Such an occurrence ($F_f$<0) is commonly observed for an upstream occlusion.

In a downstream occlusion (DSO) event the fluid pressure increases beyond an expected value (relative to the atmosphere surrounding vice 220), then $F_f$ is more positive than expected and force F 215 shows a sudden jump above expected value for $F_t$ 211 (cf. Eq. 3). The magnitude of the jump may vary according to the flow rate in tubing 111. Accordingly, Eq. 2 indicates that a sudden raise in F 215 above the expected value for $F_t$ in Eq. 3 may be due to a DSO event along the line of tubing 121.

In other scenarios, pump 120 may have a reversal cycle in which for a transitory lapse the fluid is reversed from downstream tubing 121 to upstream tubing 111. When force measurement device 230 is mechanically coupled with upstream tubing 121, a pump reversal event will create a sudden, positive increase of $F_f$ 210. Therefore a sudden, positive increase of F 215 above an expected value for $F_t$ 211 may indicate a USO, and may trigger an alarm.

Further, in scenarios where the fluid pressure remains constant, or almost constant (e.g., no infusion interruption events, or any other infusion anomalies) the total force F 215 measured is expected to follow the same behavior as tubing force $F_t$ 211 (e.g., a logarithmic decay as in Eq. 3). As the infusion progresses, it is expected that the contents of fluid container 110 will be slowly drained out, causing a slight decay in fluid pressure and therefor a natural decay in $F_f$ 210 with time. In some embodiments, the natural decay of $F_f$ 210 with time may be neglected relative to the logarithmic decay of $F_t$ 211, infusion anomalies, and the precision of force measurement device 230.

Figure 2B:
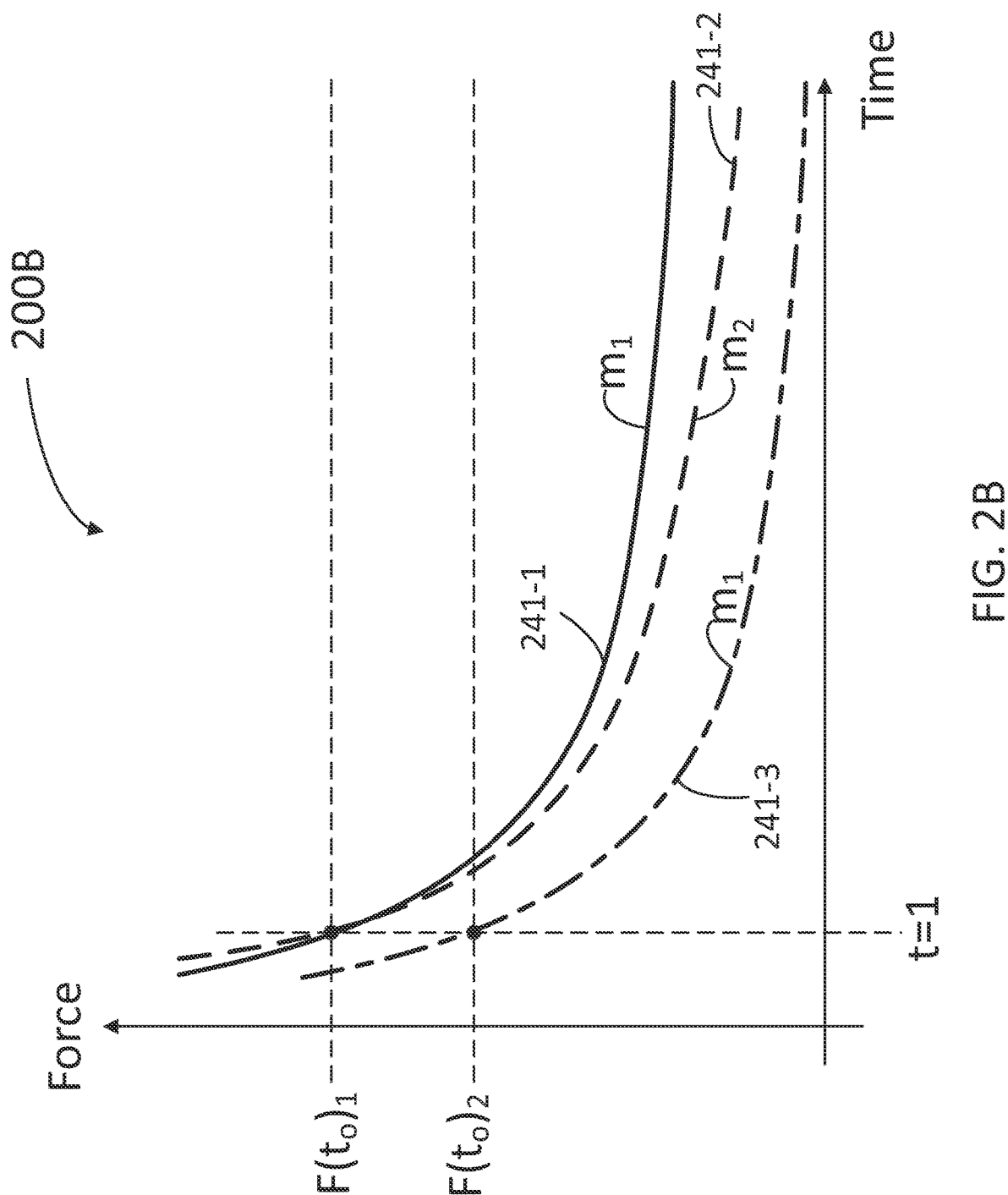
FIG. 2B illustrates a force measurement chart, according to some embodiments.

FIG. 2B illustrates a force measurement chart 200B, according to some embodiments. The ordinate (Y-axis) in chart 200B indicates a force value that may be either a total force F 215 measured with force measurement device 230, or an expected tube force $F_t$ 211 as modeled (e.g., by Eq. 3). The abscissa (X-axis) in chart 200B indicates time, normalized to arbitrary units, such that any measurement starts at time t=1. Chart 200B includes three curves 241-1, 241-2, and 241-3 (hereinafter, collectively referred to as "expected $F_t$ curves 241"), for different expected values of $F_t$ 211 as modeled by Eq. 3.

In a first curve 241-1, an initial resilient force $F(t_o)_1$ is combined with a first creep parameter $m_1$. In a second curve 241-2, initial resilient force $F(t_o)_1$ is combined with a second creep parameter $m_2$ (wherein $|m_1|<|m_2|$). In a third curve 241-3, an initial resilient force $F(t_o)_2$ is selected (wherein $F(t_o)_2 < F(t_o)_1$.

FIGS. 3A-H illustrate force measurement charts 300A-H, respectively. The ordinate (Y-axis) in charts 300A-H indicates a force value that may be either a total force F 215 measured with force measurement device 230 (e.g., data points $F_{meas}$ 321), or an expected tube force $F_t$ 211 as modeled (e.g., by Eq. 3). The abscissa (X-axis) in charts 300A-H indicate time, normalized to arbitrary units, such that any measurement starts at time t=1.

Figure 3A:
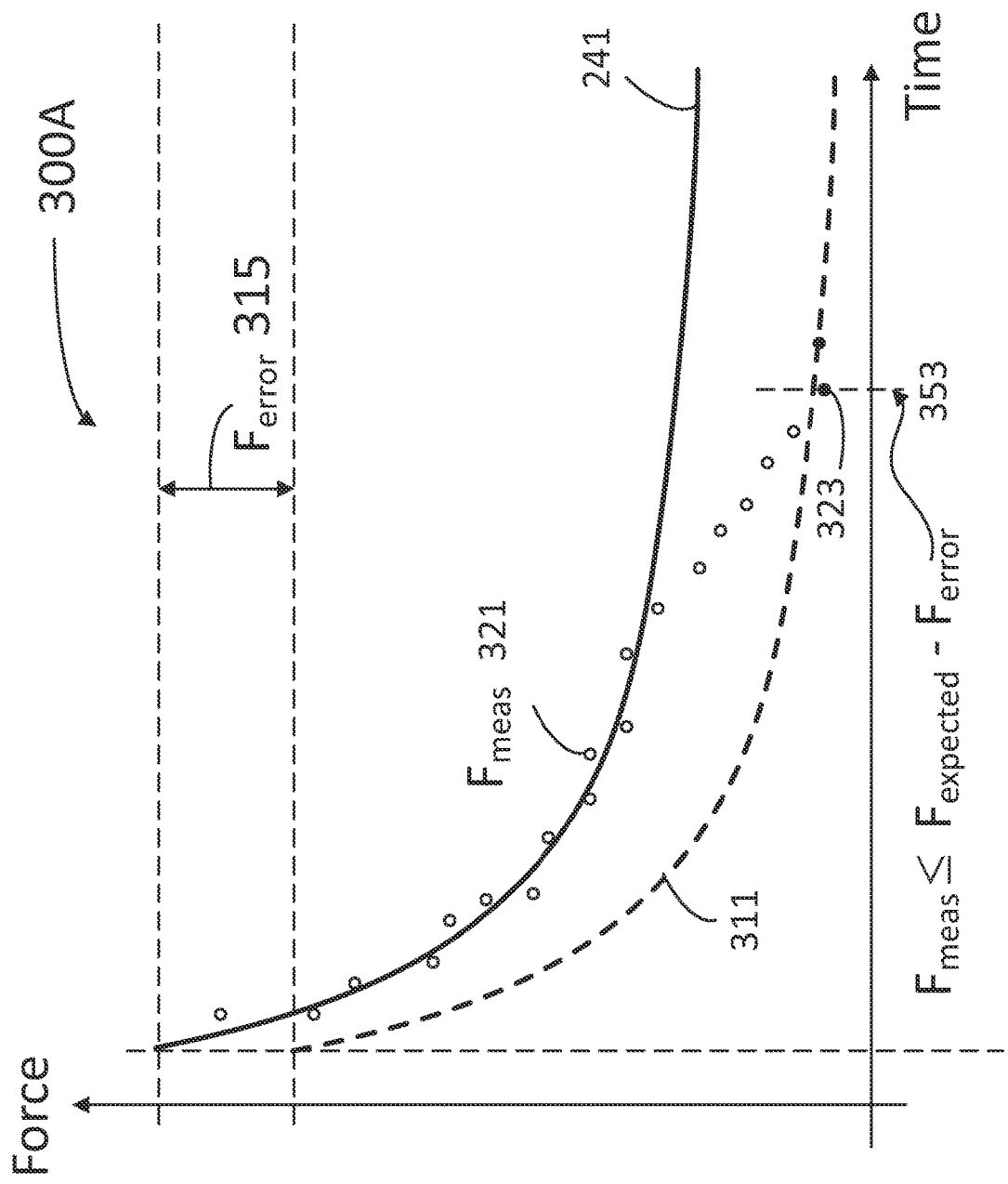
FIG. 3A illustrates a hard upstream occlusion event determined by a force measurement device in a medication infusion, according to some embodiments.

FIG. 3A illustrates a hard upstream occlusion event 353 determined by force measurement device 230 in a medication infusion, according to some embodiments. Hard USO event 353 is determined when $F_{meas}$ 321 drops below a threshold curve 311 at point 323. Threshold curve 311 is obtained by subtracting $F_{error}$ 315 from $F_{t\ expected}$ curve 241. The value of $F_{error}$ 315 may be selected by the user, or may be determined by a machine learning algorithm having access to a database including multiple data points 321 and recordings of prior hard USO events 353.

Figure 3B:
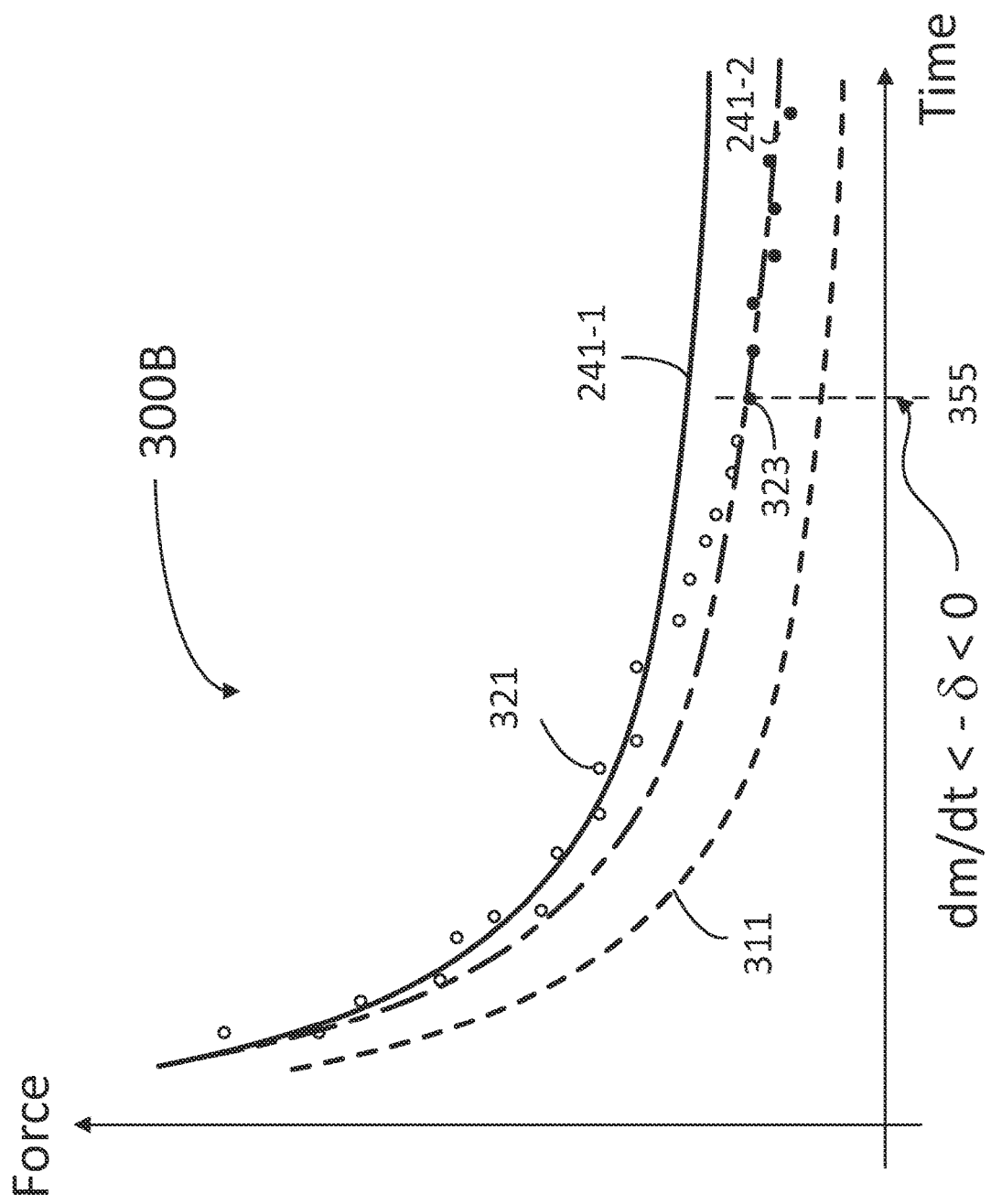
FIG. 3B illustrates a soft upstream occlusion event determined by a force measurement device in a medication infusion, according to some embodiments.

FIG. 3B illustrates a soft upstream occlusion event 355 determined by force measurement device 230 in a medication infusion, according to some embodiments. $F_{meas}$ points 321 follow first $F_t$ expected curve 241-1 until they start to slowly decrease below $F_{t\ expected}$ curve 241-1 (as of point 323). While $F_{meas}$ points 321 do not cross below threshold curve 311, they become consistently aligned with $F_{t\ expected}$ curve 241-2 having a creep parameter $m_2$ that is more negative than $m_1$ (cf. FIG. 2B). Occlusion detection system 100 may determine that a soft USO event 355 has occurred when a rate of change of parameter m is lower than a pre-selected threshold, $-\delta$, $(dm/dt<-\delta<0)$.

Several data points 321, departing from curve 241-1 before an alarm is set at point 355 is triggered and curve 241-2 is obtained in a new regression. Accordingly, in some embodiments a lag of the regression relative to the force measurement may be beneficial to ensure that the deviation from curve 241-1 is not a fluctuation.

Figure 3C:
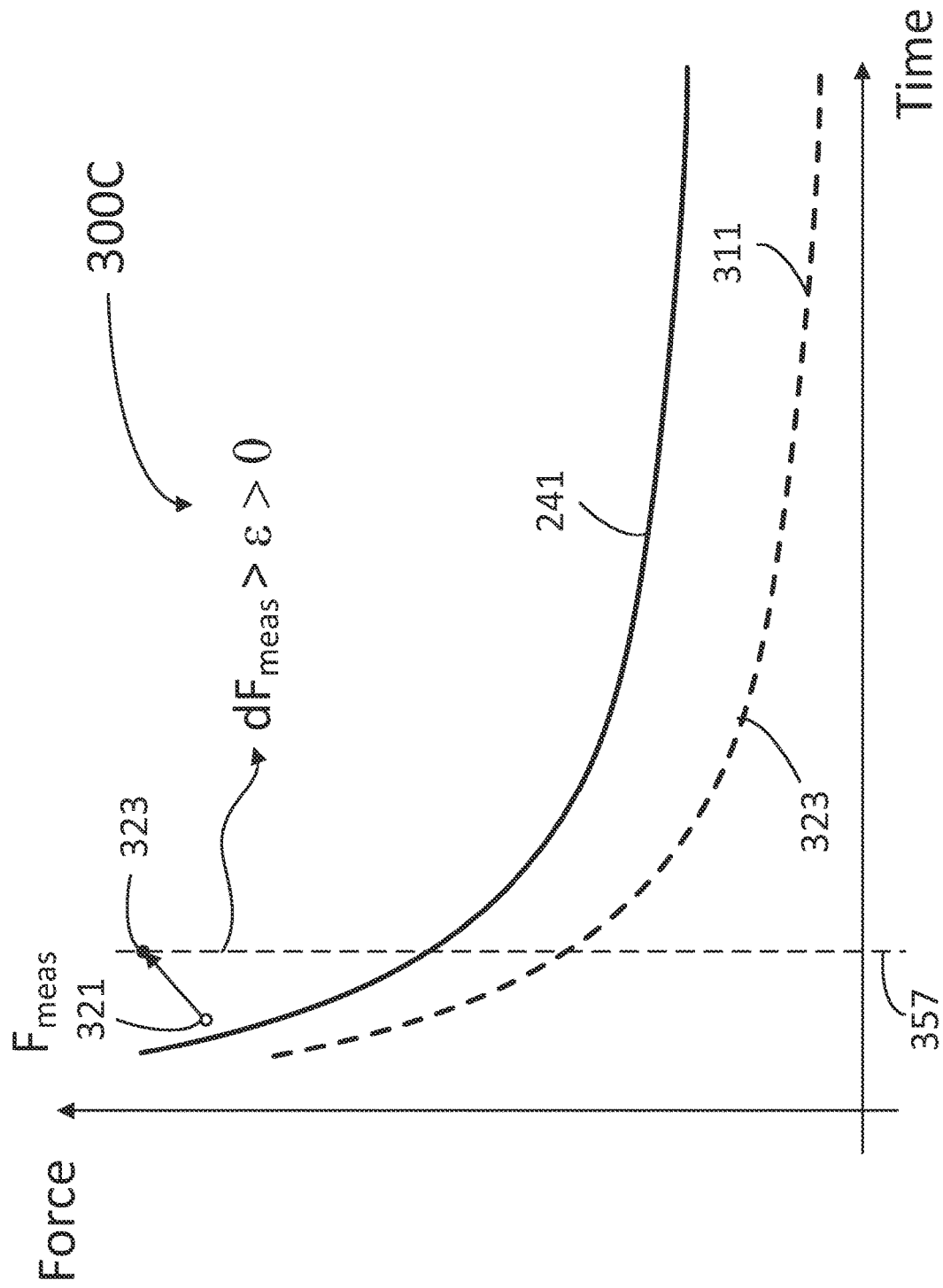
FIG. 3C illustrates a pump reversal event determined by a force measurement device at the start of a medication infusion, according to some embodiments.

FIG. 3C illustrates a pump reversal event 357 determined by force measurement device 230 at the start of a medication infusion, according to some embodiments. In embodiments as disclosed herein, pump reversal may be induced purposely to determine the existence of an USO, e.g., a rapid increase in pressure under pump reversal may indicate USO. Pump reversal event 357 may be characterized by a sudden increase in $F_{meas}$ 321 ($dF_{meas}/dt>0$), which in some embodiments may occur at the start of the medication infusion (cf. point 323). In some embodiments, occlusion detection system 100 introduces a pump reversal event 357 at measurement point 323, and when a rate of change of measured force $dF_{meas}/dt$ exceeds a pre-selected threshold, $\Sigma$ ($dF_{meas}/dt>\Sigma$) generates an alarm/alert. A value of $dF_{meas}/dt$ in pump reversal event 357 may be enhanced dramatically when an occlusion (e.g., a soft occlusion) is present upstream of force measurement device 230. Indeed, when such is the case, it is seen that when pump 120 operates in the forward direction there is a reduction in $F_{meas}$ as the fluid pressure drops (cf. Eq. 1), which becomes an increase in $F_{meas}$ due to a sudden fluid pressure raise in pump reversal event 357. Accordingly, in some embodiments, a pressure increase (as determined by a force $F_{meas}$ increase) during a pump reversal event 357 may also indicate the present of an upstream occlusion (e.g., soft or hard). Further, in some embodiments, at the start of the infusion process, a pump reversal event may be induced briefly to determine whether $dF_{meas}/dt$ increases beyond a pre-determined threshold, thereby revealing the presence of an upstream occlusion. When the induced pump reversal reveals a dovetailing of $F_{meas}$ ($dF_{meas}/dt$ less than the pre-selected threshold, or zero), it may be determined that no occlusion is present.

Figure 3D:
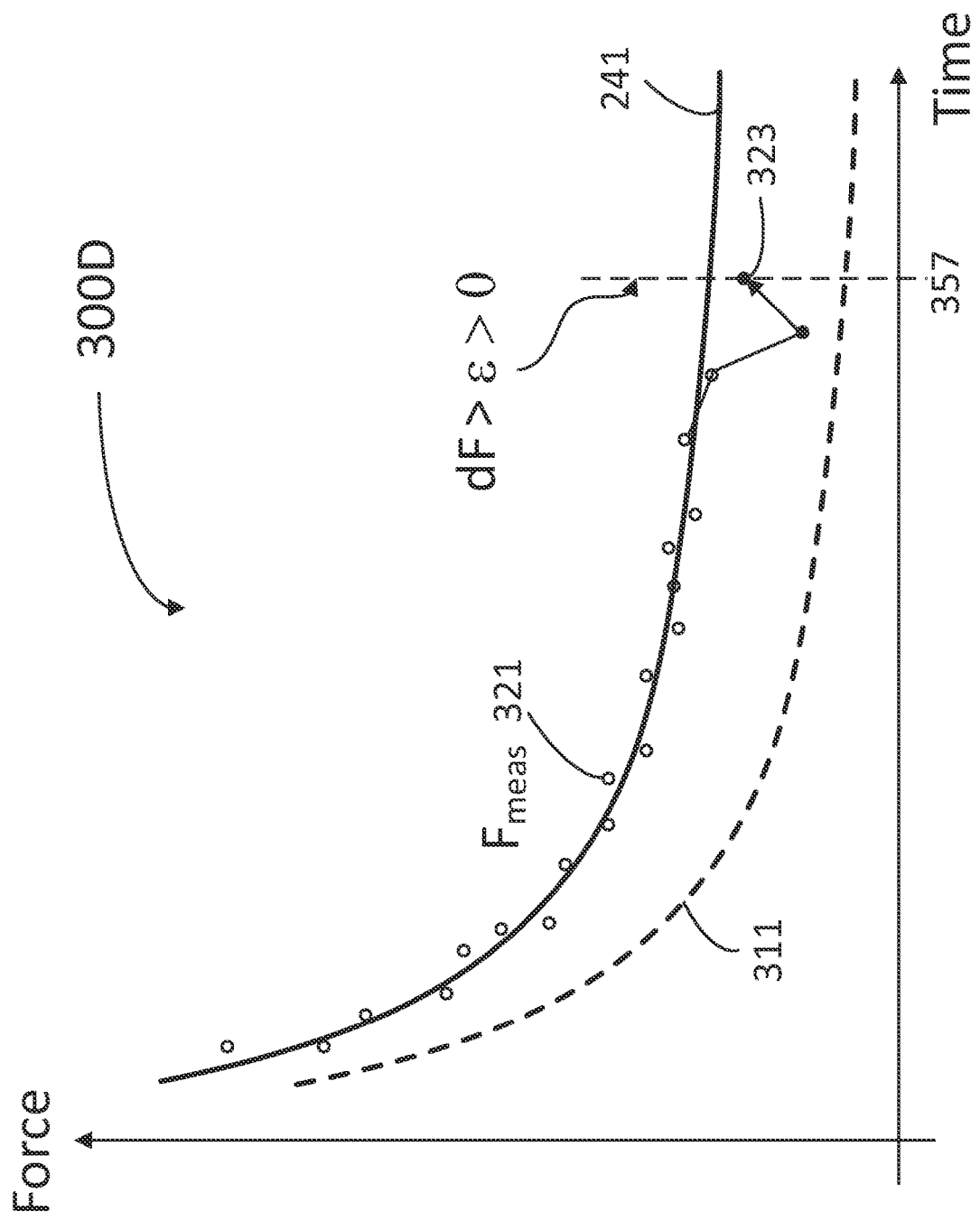
FIG. 3D illustrates a pump reversal event induced by the fluid displacement system in the middle of a medication infusion, to confirm the existence of an occlusion according to some embodiments.

FIG. 3D illustrates a pump reversal event 357 determined by force measurement device 230 in the middle of a medication infusion, according to some embodiments. Accordingly, $F_{meas}$ 323 associated with $dF_{meas}/dt>+>0$ occurs further down the medication infusion process.

Figure 3E:
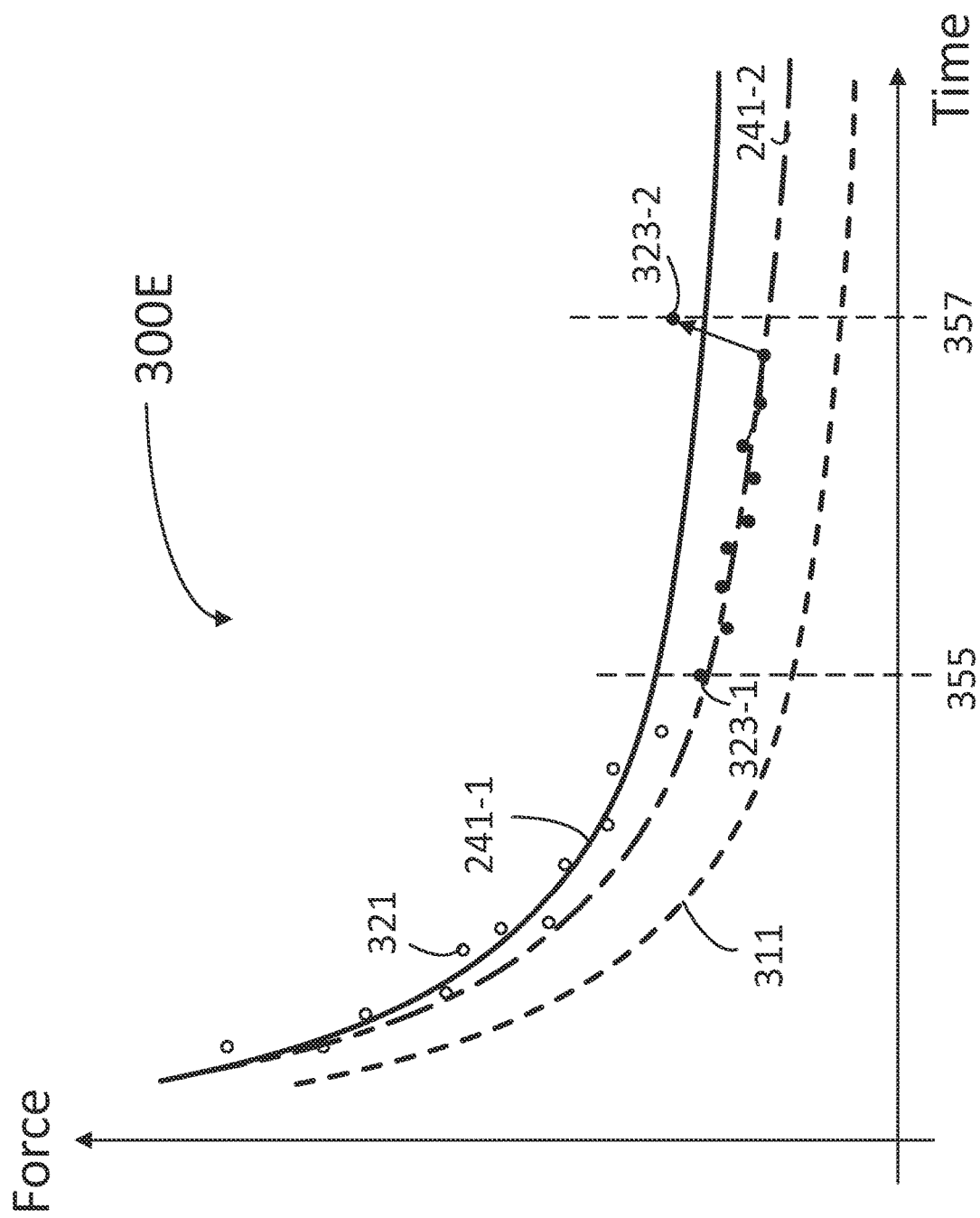
FIG. 3E illustrates a pump reversal event subsequent to a soft upstream occlusion event determined by a force measurement device in the middle of a medication infusion, according to some embodiments.

FIG. 3E illustrates a pump reversal event 357 subsequent to soft USO event 355 determined by force measurement device 230 in the middle of a medication infusion, according to some embodiments. Soft USO event 355 occurs at measurement point 323-1 when $dm/dt<-\delta<0$, so that measurement points 321 follow curve Ft-expected 241-2 up to measurement point 323-2, when $dF_{meas}/dt>+8>0$.

Figure 3F:
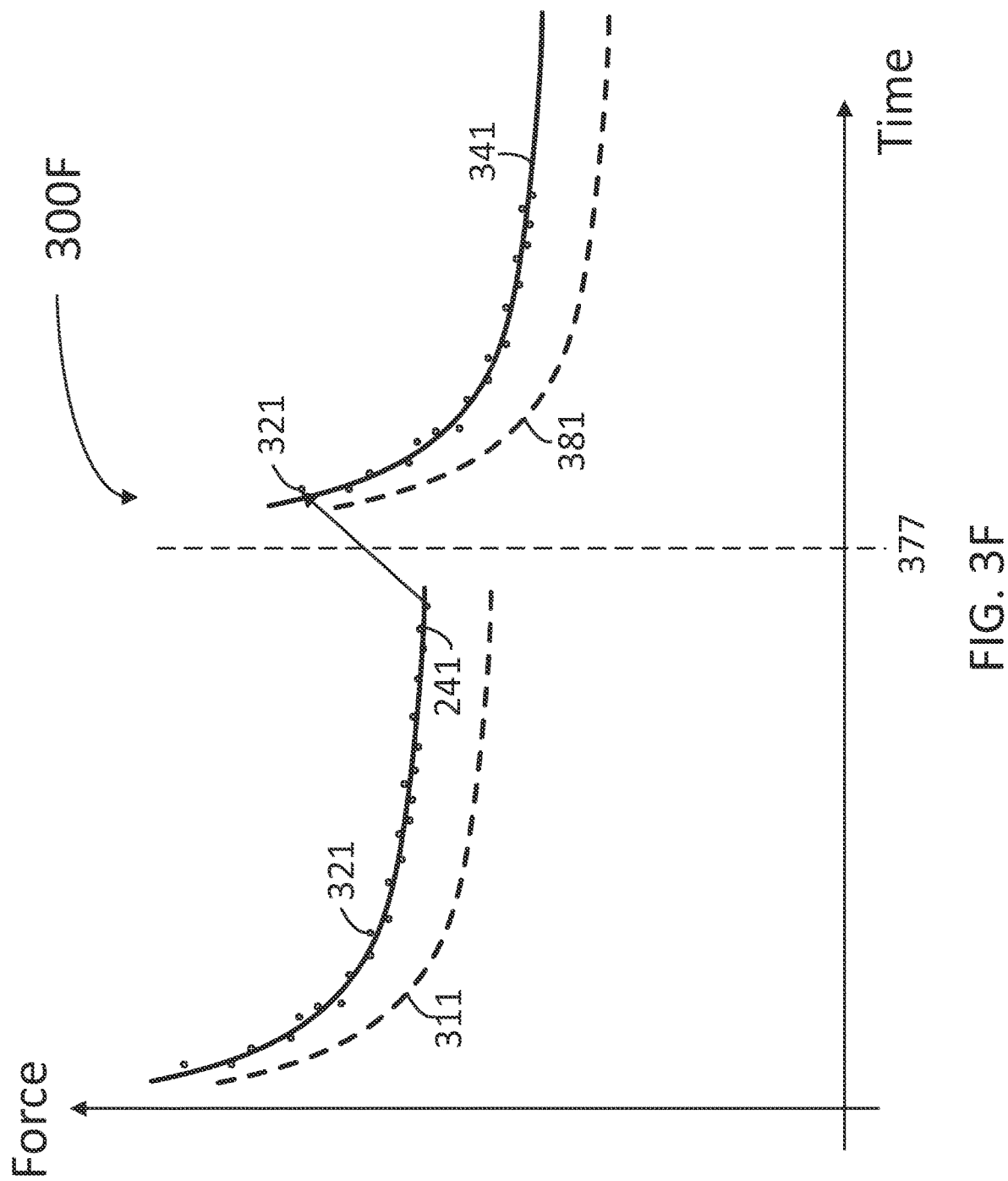
FIG. 3F illustrates an open-close door and restart event determined by a force measurement device in a medication infusion, according to some embodiments.

FIG. 3F illustrates an infusion interrupt event 377 determined by force measurement device 230 in a medication infusion, according to some embodiments. Infusion interrupt event 377 may be associated with an infusion malfunction or anomaly, or any interruption caused by medical personnel opening-closing and restarting the medication infusion process. During infusion interrupt event 377, a large change in $F_{meas}$ value may be observed at point 321 over a short span of time. The change in $F_{meas}$ value may be positive (as illustrated) or negative. However, as chart 300F illustrates, measurement points 321 after infusion interrupt event 377 follow closely a new curve $F_t$ expected 341 and remain well above a new threshold curve 381 (wherein threshold curve 381 is obtained by subtracting $F_{error}$ 315 from $F_{t\ expected}$ 341. In some embodiments, the system is configured to recalculate $F_{t\ expected}$ curve 341 using the first data point 321 (or the first few data points 321) after infusion interrupt event 377. In some embodiments, when the system detects a large change (e.g., an increase) in $F_{meas}$, then curve $F_{t\ expected}$ 341 is recalculated using a different (e.g., larger) value for initial force $F(t_{377})$ and a re-calibrated value for time, t, while maintaining the same value for the stress relaxation (m). For example, a regression formula for curve $F_t$ expected 341 may be:

$$F_t = F(t_{377}) + m \cdot \ln(t - t_{377}) \quad (4)$$

Wherein $t_{377}$ is the time at which infusion interrupt event 377 took place.

In the case when infusion interrupt event 377 is due to an open-close and restart event, the initial force $F(t_{377})$ may include a natural resiliency of the infusion tubing (e.g., upstream tubing 111) to its un-deformed shape when released from vice 220.

Figure 3G:
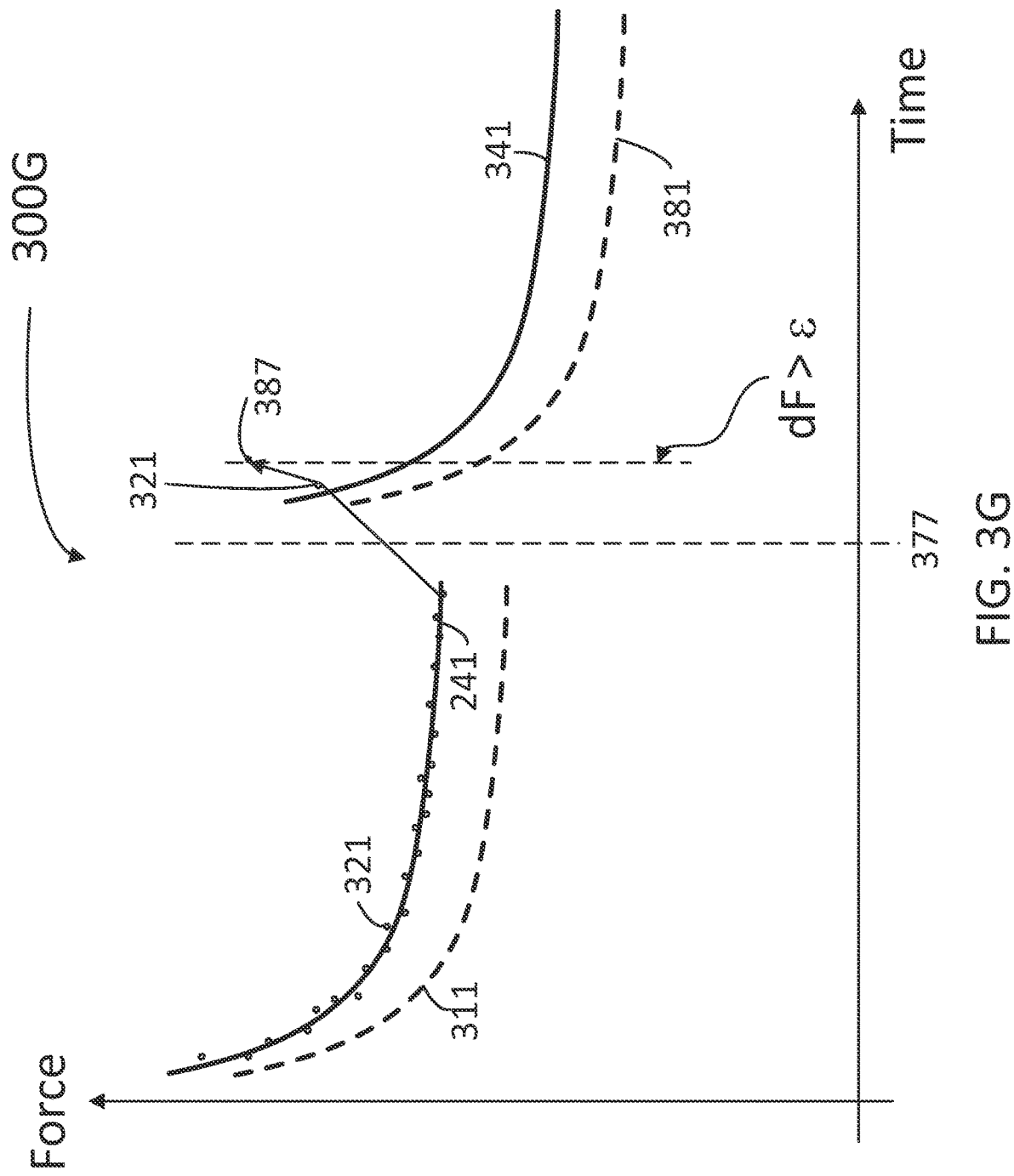
FIG. 3G illustrates an open-close door and restart event followed by a pump reversal event determined by a force measurement device in the middle of a medication infusion, according to some embodiments.

FIG. 3G illustrates an infusion interrupt event 377 followed by a pump reversal event 387 shortly after restart, determined by force measurement device 230 in the middle of a medication infusion, according to some embodiments. Accordingly, pump reversal event 387 illustrates an abnormal increase, $(dF/dt>+\varepsilon>0)$, in $F_{meas}$ even after curves 341 and 381 are calculated.

Figure 3H:
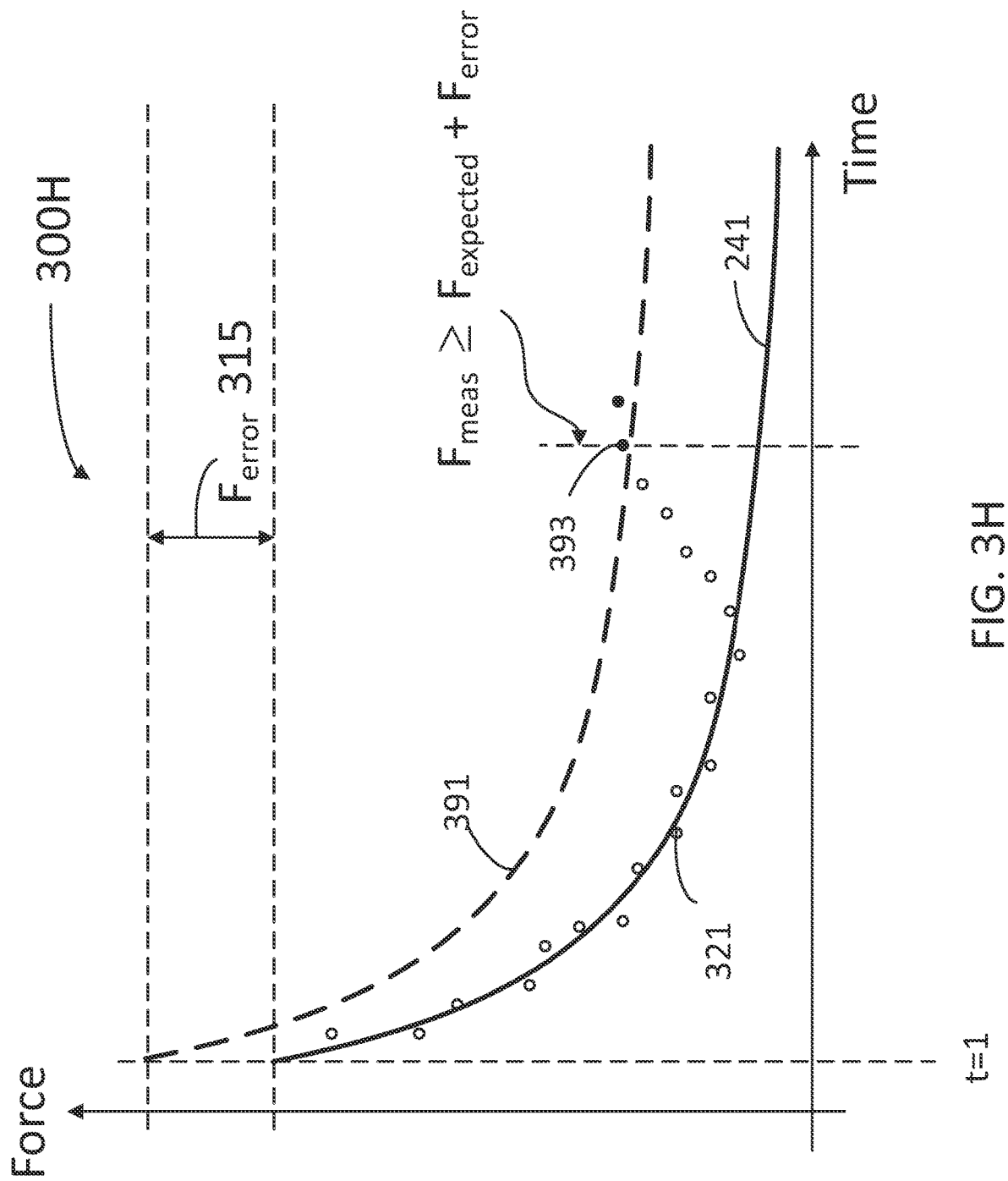
FIG. 3H illustrates a downstream occlusion event determined by a force measurement device in a medication infusion, according to some embodiments.

FIG. 3H illustrates a downstream occlusion (DSO) event 393 determined by force measurement device 230 in a medication infusion, according to some embodiments. A DSO event 393 is determined when $F_{meas}$ 321 jumps above a threshold curve 391 at point 393. Threshold curve 391 is obtained by adding $F_{error}$ 315 to $F_t$ expected curve 241. The value of $F_{error}$ 315 may be selected by the user, or may be determined by recordings of prior DSO events 393.

Figure 4:
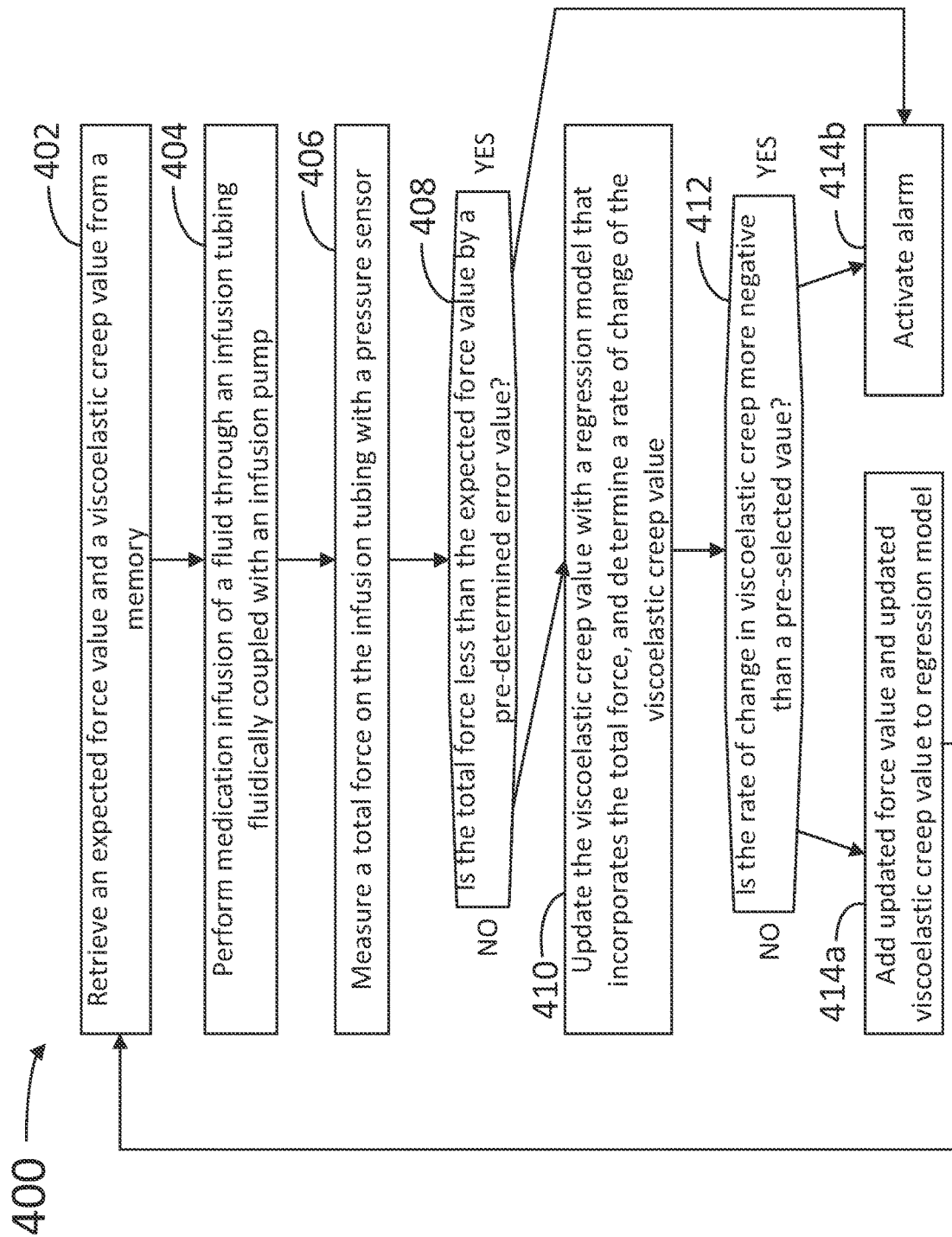
FIG. 4 illustrates a flowchart with steps in a method for detecting an occlusion event in an infusion architecture, according to some embodiments.

FIG. 4 illustrates a flowchart with steps in a method 400 for detecting an occlusion event in an infusion architecture, according to some embodiments. At least some of the steps in method 400 may be performed by a system having a processor executing commands stored in a memory of the computer (e.g., occlusion detection system 100, processor 161, and memory 162). The system may include a force measurement device providing data to and receiving commands from the processor (e.g., force measurement device 130). The force measurement device may be coupled to an infusion architecture including a container, an upstream tubing fluidically coupling the container with an infusion pump, and a downstream tubing fluidically coupling the infusion pump to a patient (e.g., infusion architecture 10, upstream tubing 111, infusion pump 120, downstream tubing 121, patient 150). The force medication architecture may be communicably coupled with an alarm, so as to prompt medical personnel or equipment to handle an occlusion event upstream or downstream from the pump, or a pump reversal event (e.g., alarm 170). Further, steps as disclosed in method 400 may include retrieving, editing, and/or storing files in a database that is part of, or is communicably coupled to, the computer (e.g., database 180). Methods consistent with the present disclosure may include at least some, but not all of the steps illustrated in method 400, performed in a different sequence. Furthermore, methods consistent with the present disclosure may include at least two or more steps as in method 400, performed overlapping in time, or almost simultaneously.

Step 402 includes retrieving an expected force value and a stress relaxation value from the memory. The memory may include a regression model for the expected force value, the regression model being dependent on parameters such as the stress relaxation and an initial force value offset. In some embodiments, the regression model includes a mathematical expression for the expected tubing force as a function of time (cf. Eq. 3). Accordingly, in some embodiments the regression includes a logarithmically decaying function of time, controlled by the stress relaxation of the tubing material.

Step 404 includes performing a medication infusion of a fluid through an infusion tubing fluidically coupled with the infusion pump. In some embodiments, the infusion tubing includes the upstream tubing and the downstream tubing, fluidically coupled with one another via the infusion pump.

Step 406 includes measuring a total force on the infusion tubing with a pressure sensor. In some embodiments, step 406 includes squeezing the infusion tubing against a pressure sensor in the force measurement device.

Step 408 includes determining whether the updated force value is less than the expected force value by a pre-determined error value (e.g., $F_{error}$ 315, cf. FIG. 3A).

Step 410 includes updating the stress relaxation value with a regression model that incorporates the total force (cf. Eq. 3), and determining a rate of change of the stress relaxation value (dm/dt).

Step 412 includes determining whether the rate of change in the stress relaxation is more negative than a pre-selected value, $\delta$ (dm/dt<$-\delta$<0).

When the measured force is not less than the expected force and the change in stress relaxation value is not negative according to step 408, step 414a includes adding the updated force value and the updated stress relaxation value to the regression model. The method may be repeated from step 402 until the infusion process is complete.

When the measured force is less than the expected force, or when the change in stress relaxation is negative according to step 408, step 414b includes activating the alarm.

Figure 5:
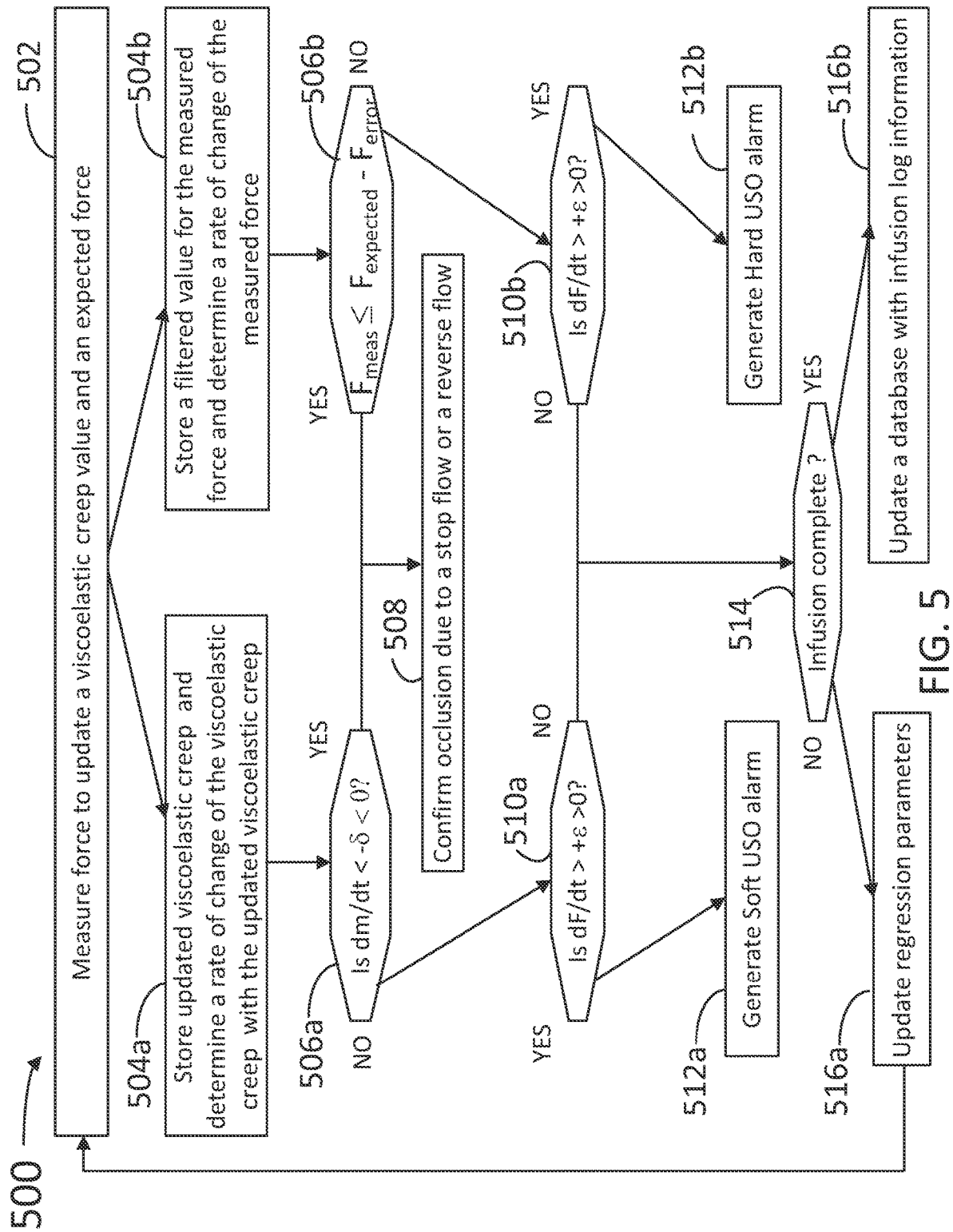
FIG. 5 illustrates a flowchart with steps in a method for detecting a pump reverse event in an infusion architecture, according to some embodiments.

FIG. 5 illustrates a flowchart with steps in a method 500 for detecting an upstream occlusion using the disclosed method and including intentional pump reversal in an infusion architecture, according to some embodiments. At least some of the steps in method 500 may be performed by a system having a processor executing commands stored in a memory of the computer (e.g., occlusion detection system 100, processor 161, and memory 162). The system may include a force measurement device providing data to and receiving commands from the processor (e.g., force measurement device 130). The force measurement device may be coupled to an infusion architecture including a container, an upstream tubing fluidically coupling the container with an infusion pump, and a downstream tubing fluidically coupling the infusion pump to a patient (e.g., infusion architecture 10, upstream tubing 111, infusion pump 120, downstream tubing 121, patient 150). The force medication architecture may be communicably coupled with an alarm, so as to prompt medical personnel or equipment to handle an occlusion event upstream or downstream from the pump, or a pump reversal event (e.g., alarm 170). Further, steps as disclosed in method 500 may include retrieving, editing, and/or storing files in a database that is part of, or is communicably coupled to, the computer (e.g., database 180). Methods consistent with the present disclosure may include at least some, but not all of the steps illustrated in method 500, performed in a different sequence. Furthermore, methods consistent with the present disclosure may include at least two or more steps as in method 500, performed overlapping in time, or almost simultaneously.

Step 502 includes measuring a total force from the tubing to update a stress relaxation value and an expected force.

Step 504a includes storing the updated stress relaxation value and determining a rate of change of the stress relaxation value (dm/dt). Step 504b includes storing a filtered value for the measured force and determining a rate of change of the measured force (dF/dt). In some embodiments, step 504a includes filtering a force measurement provided by the force measurement device to smooth out system fluctuations. Some examples in step 504a may include determining a moving average of a selected number of measurement points, or applying a more sophisticated filter to the data, e.g., a Kalman filter, a digital filter, or any other predictor of a true force value given the measured force value $F_{meas}$ and a statistical analysis of prior measurement fluctuations.

Step 506a includes determining whether the absolute value of the rate of change of the stress relaxation value is greater than a pre-determined threshold, $\delta$ (dm/dt<$-\delta$<0). Step 506b includes determining whether the measured total force from the tubing is lower than the expected force by a pre-determined threshold, $F_{error}$ ($F_{meas}<F_{expected}-F_{error}$).

Step 508 includes confirming an occlusion due to a stop flow and reversal of flow when step 506a determines that |dm/dt|>$\delta$, or when step 506b determines that $F_{meas}<F_{expected}-F_{error}$.

Step 510a includes determining whether dF/dt is larger than a pre-determined threshold, $\varepsilon$ (dF/dt+$\varepsilon$>0) when dm/dt<$-\delta$<0, according to step 506a. Step 510b includes determining whether dF/dt is larger than $\varepsilon$ (dF/dt+$\varepsilon$>0), when $F_{meas}>F_{expected}-F_{error}$, according to step 506b.

Step 512a includes generating a soft USO alarm when step 510a determines that, dF/dt+$\varepsilon$>0. Step 512b includes generating a hard USO alarm when step 510b determines that dF/dt+$\varepsilon$>0.

Step 514 includes determining whether the infusion process is complete when dF/dt>+$\varepsilon$ according to steps 510a and 510b.

Step 516a includes updating the regression parameters and repeating method 500 from step 502 when the infusion process is not complete. Step 516b includes updating the database with infusion log information. In some embodiments, step 516b includes storing the measured force and the stress relaxation value in the database, wherein the database includes multiple measured force values and multiple stress relaxation values associated with an infusion condition (e.g., upstream occlusion, downstream occlusion, pump reversal, infusion interrupt, and the like), and wherein updating the regression model comprises training the regression model on the multiple total force values and the multiple stress relaxation values.

Figure 6:
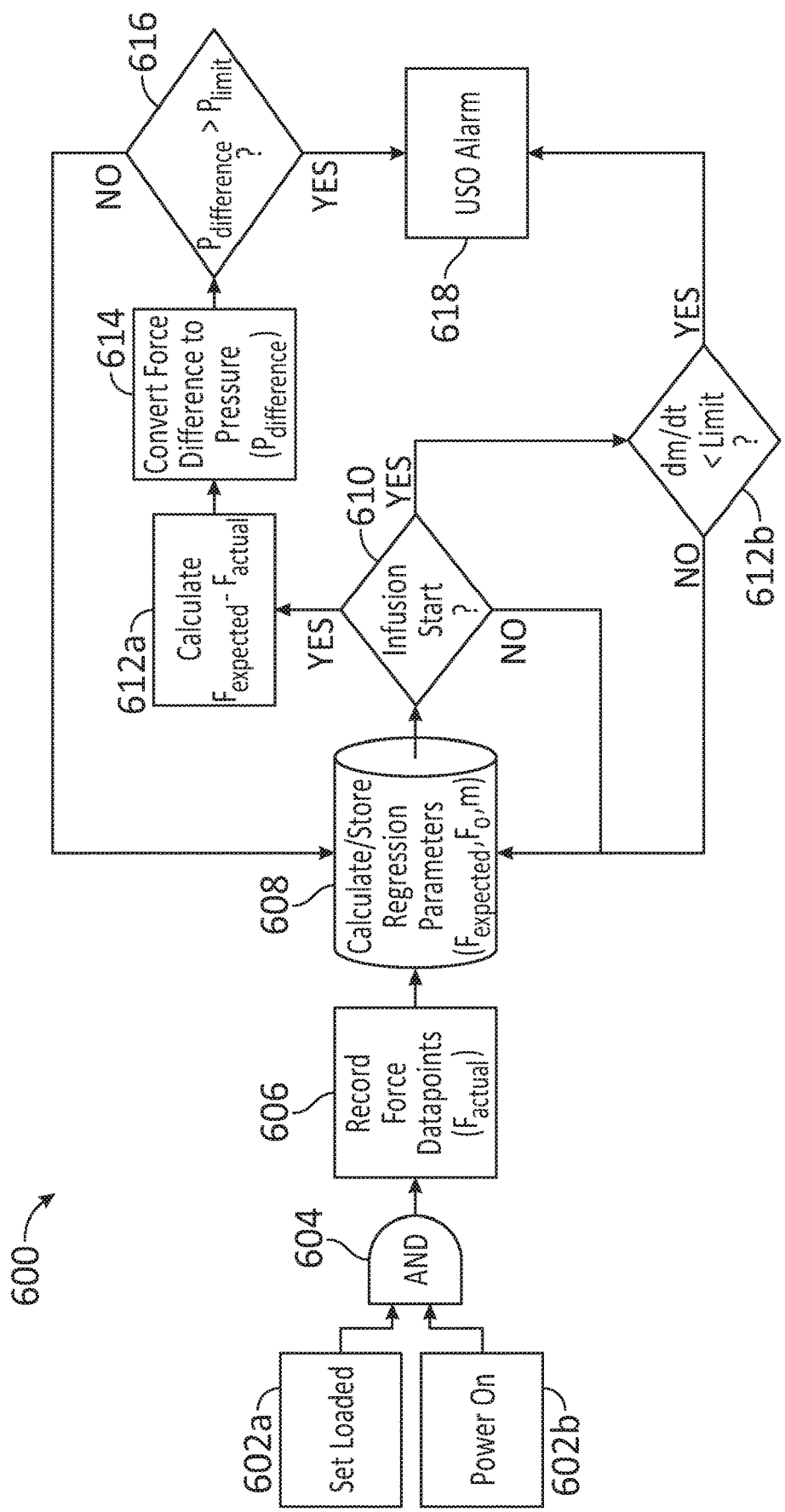
FIG. 6 illustrates a flowchart with steps in a method for detecting a high level upstream occlusion in an infusion architecture, according to some embodiments.

FIG. 6 illustrates a "low detail" flowchart with steps in a method for detecting an upstream occlusion in an infusion architecture, according to some embodiments. At least some of the steps in method 600 may be performed by a system having a processor executing commands stored in a memory of the computer (e.g., occlusion detection system 100, processor 161, and memory 162). The system may include a force measurement device providing data to and receiving commands from the processor (e.g., force measurement device 130). The force measurement device may be coupled to an infusion architecture including a container, an upstream tubing fluidically coupling the container with an infusion pump, and a downstream tubing fluidically coupling the infusion pump to a patient (e.g., infusion architecture 10, upstream tubing 111, infusion pump 120, downstream tubing 121, patient 150). The force medication architecture may be communicably coupled with an alarm, so as to prompt medical personnel or equipment to handle an occlusion event upstream or downstream from the pump, or a pump reversal event (e.g., alarm 170). Further, steps as disclosed in method 600 may include retrieving, editing, and/or storing files in a database that is part of, or is communicably coupled to, the computer (e.g., database 180). Methods consistent with the present disclosure may include at least some, but not all of the steps illustrated in method 600, performed in a different sequence. Furthermore, methods consistent with the present disclosure may include at least two or more steps as in method 600, performed overlapping in time, or almost simultaneously.

Steps 602a and 602b include loading and powering 'on' an IV infusion pump set including tubing, a pump, and a pressure sensor, as disclosed herein. Step 604 includes verifying that steps 602a and 602b have been completed. Step 606 includes measuring a force data point, $F_{actual}$. Step 608 includes calculating and storing regression parameters such as $F_{expected}$, $F_o$, and m. Step 610 includes verifying that the infusion process has started. If the infusion process has not started, the method returns to step 608.

When the infusion process has started, step 612a includes calculating the difference $F_{expected}-F_{actual}$. Step 614 includes converting force difference to pressure difference ($P_{difference}$). Step 616 includes determining whether $P_{difference}$ is greater than a pre-selected $P_{limit}$ value. If $P_{difference}$ is greater than $P_{limit}$, step 618 includes activating the USO alarm, otherwise the method returns to step 608. When the infusion process has started, step 612b includes verifying whether dm/dt<limit, where "limit" is a pre-selected, negative, threshold. When dm/dt<limit, step 618 includes activating the USO alarm, otherwise the method returns to step 608.

Figure 7:
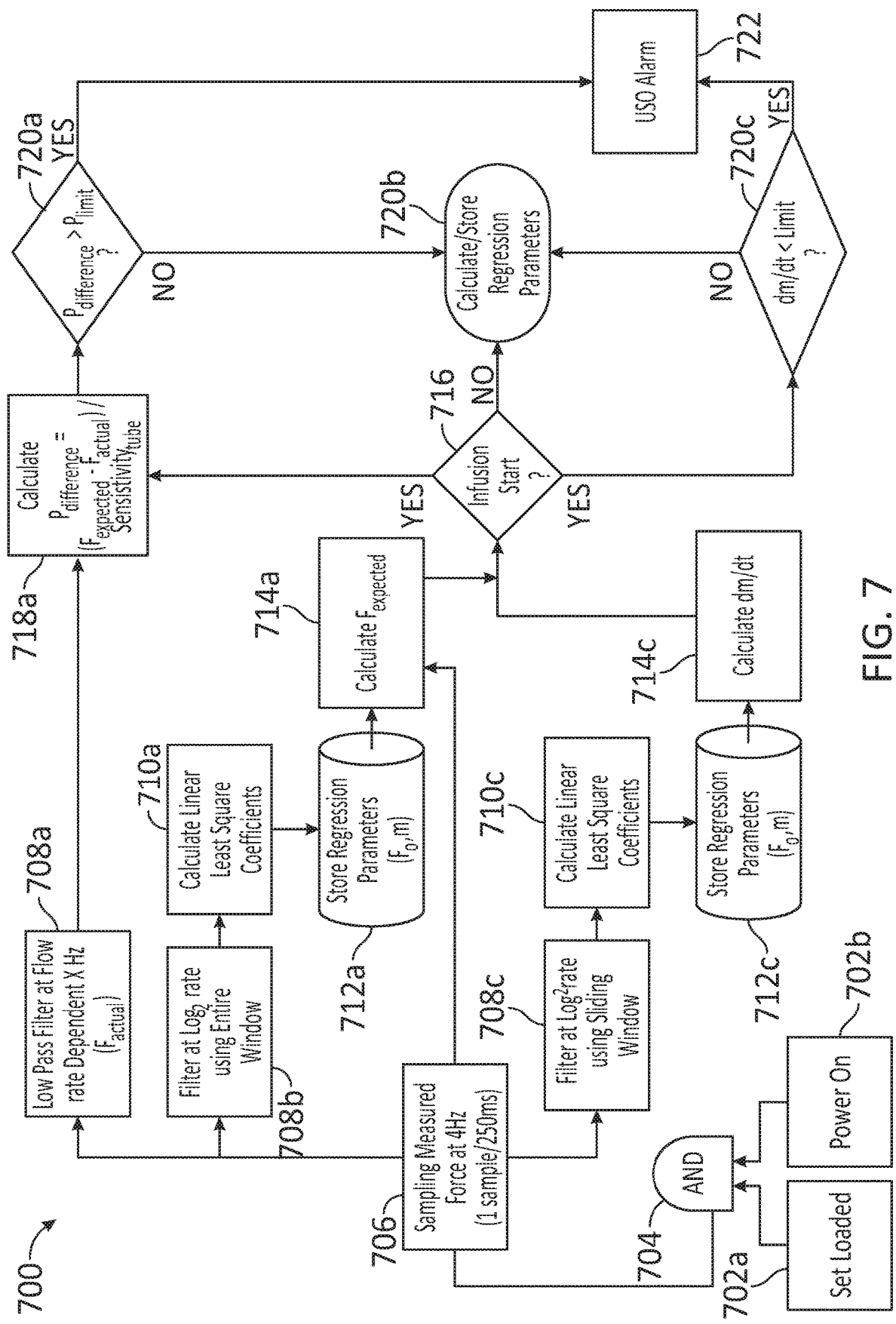
FIG. 7 illustrates a flowchart with steps in a method for detecting a medium level upstream occlusion in an infusion architecture, according to some embodiments.

FIG. 7 illustrates a more detailed flowchart with steps in a method for detecting an upstream occlusion in an infusion architecture, according to some embodiments. At least some of the steps in method 700 may be performed by a system having a processor executing commands stored in a memory of the computer (e.g., occlusion detection system 100, processor 161, and memory 162). The system may include a force measurement device providing data to and receiving commands from the processor (e.g., force measurement device 130). The force measurement device may be coupled to an infusion architecture including a container, an upstream tubing fluidically coupling the container with an infusion pump, and a downstream tubing fluidically coupling the infusion pump to a patient (e.g., infusion architecture 10, upstream tubing 111, infusion pump 120, downstream tubing 121, patient 150). The force medication architecture may be communicably coupled with an alarm, so as to prompt medical personnel or equipment to handle an occlusion event upstream or downstream from the pump, or a pump reversal event (e.g., alarm 170). Further, steps as disclosed in method 700 may include retrieving, editing, and/or storing files in a database that is part of, or is communicably coupled to, the computer (e.g., database 180). Methods consistent with the present disclosure may include at least some, but not all of the steps illustrated in method 700, performed in a different sequence. Furthermore, methods consistent with the present disclosure may include at least two or more steps as in method 700, performed overlapping in time, or almost simultaneously.

Steps 702a and 702b include loading and powering 'on' an IV infusion pump set including tubing, a pump, and a pressure sensor, as disclosed herein. Step 704 includes verifying that steps 702a and 702b have been completed. Step 706 includes measuring a force at approximately 4 hertz (Hz=1 measurement per second).

Step 708a includes applying a low pass filter with a flow rate dependent frequency response to obtain $F_{actual}$. Step 708b includes applying a filter at $\log_2$ of the flow rate using data from the entire sample window (e.g., all samples thus far collected). The time window/sample size may be variable. In some embodiments, a continuous sampling at $\log_2$ rate is maintained until the tubing is removed from the pump (e.g., removed from the force sensor). Step 708c includes filter at $\log_2$ of the flow rate using a sliding window. Step 710a includes calculating linear least square coefficients of the filtered $\log_2$ flow rate data with the entire window (step 708b). Step 712a includes storing regression parameters from step 710a (e.g., $F_o$, m), and step 714a includes calculating $F_{expected}$ from the regression parameters of step 712a.

Step 710c includes calculating linear least square coefficients of the filtered $\log_2$ flow rate sampling with a sliding window (step 708c). Step 712c includes storing regression parameters (e.g., $F_o$, m) from step 710c, and step 714c includes calculating dm/dt using the regression parameters from step 712c.

Step 716 includes verifying whether the infusion process has started. When the infusion process has started, Step 718a includes calculating $P_{difference}=(F_{expected}-F_{actual})$/Sensitivity$_{Tube}$ and step 720c includes determining whether dm/dt is lower than a negative, pre-selected limit value (dm/dt<$L_{limit}$). When the infusion has not started, or dm/dt is not less than the negative, pre-selected limit value, step 720b includes calculating and storing the regression parameters.

Step 720a includes determining whether $P_{difference}$ from step 718a is less than a pre-selected $P_{limit}$ value. If it is not, then the method proceeds with step 720b. If $P_{difference}$ is greater than $P_{limit}$ (step 720a), or if dm/dt<limit (step 720c), step 722 includes activating the USO alarm.

Figure 8:
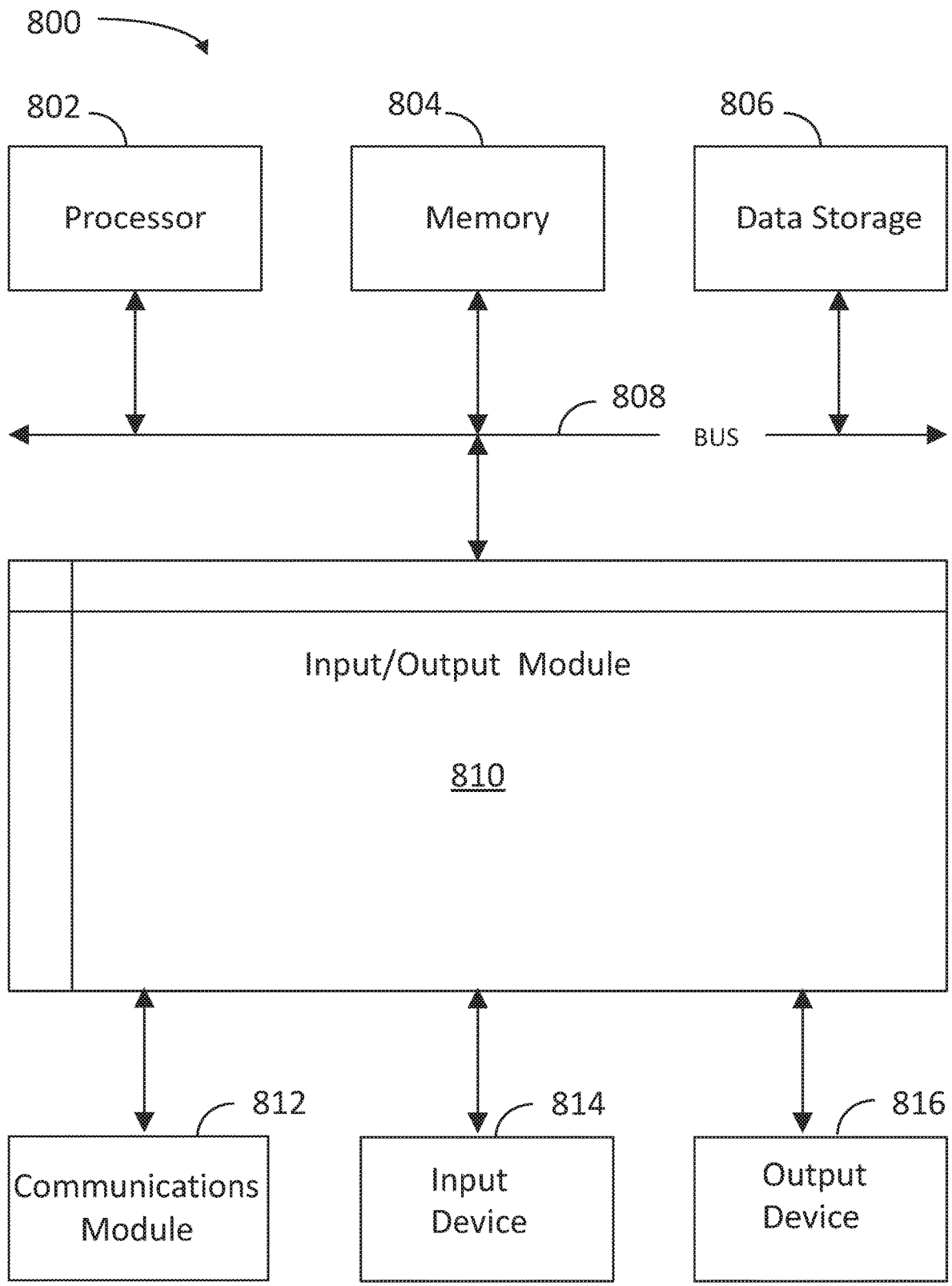
FIG. 8 is a block diagram illustrating an example computer system for distributed medication dispensing, according to some embodiments.

FIG. 8 is a block diagram illustrating an example computer system 800 with which the methods and steps illustrated in methods 400-700 can be implemented, according to some embodiments. In certain aspects, computer system 800 can be implemented using hardware or a combination of software and hardware, either in a dedicated server, integrated into another entity, or distributed across multiple entities.

Computer system 800 includes a bus 808 or other communication mechanism for communicating information, and a processor 802 coupled with bus 808 for processing information. By way of example, computer system 800 can be implemented with one or more processors 802. Processor 802 can be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information. In some embodiments, processor 802 may include modules and circuits configured as a 'placing' tool or engine, or a 'routing' tool or engine, to place devices and route channels in a circuit layout, respectively and as disclosed herein.

Computer system 800 includes, in addition to hardware, code that creates an execution environment for the computer program in question, e.g., code that constitutes processor firmware, a protocol stack, a database management system, an operating system, or a combination of one or more of them stored in an included memory 804, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 808 for storing information and instructions to be executed by processor 802. Processor 802 and memory 804 can be supplemented by, or incorporated in, special purpose logic circuitry.

The instructions may be stored in memory 804 and implemented in one or more computer program products, i.e., one or more modules of computer program instructions encoded on a computer readable medium for execution by, or to control the operation of, the computer system 800, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PUP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, Wirth languages, embeddable languages, and xml-based languages. Memory 804 may also be used for storing temporary variable or other intermediate information during execution of instructions to be executed by processor 802.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 800 further includes a data storage device 806, such as a magnetic disk or optical disk, coupled to bus 808 for storing information and instructions.

Computer system 800 is coupled via input/output module 810 to various devices. The input/output module 810 is any input/output module. Example input/output modules 810 include data ports, such as USB ports. The input/output module 810 is configured to connect to a communications module 812. Example communications modules 812 include networking interface cards, such as Ethernet cards and modems. In certain aspects, the input/output module 810 is configured to connect to a plurality of devices, such as an input device 814 and/or an output device 816. Example input devices 814 include a keyboard and a pointing device, e.g., a mouse or a trackball, by which a user can provide input to the computer system 800. Other kinds of input devices 814 are used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 816 include display devices, such as a LED (light emitting diode), CRT (cathode ray tube), or LCD (liquid crystal display) screen, for displaying information to the user.

Methods as disclosed herein may be performed by computer system 800 in response to processor 802 executing one or more sequences of one or more instructions contained in memory 804. Such instructions may be read into memory 804 from another machine-readable medium, such as data storage device 806. Execution of the sequences of instructions contained in main memory 804 causes processor 802 to perform the process steps described herein (e.g., as in methods 400-700). One or more processors in a multi-processing arrangement may also be employed to execute the sequences of instructions contained in memory 804. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication network can include, for example, any one or more of a personal area network (PAN), a local area network (LAN), a campus area network (CAN), a metropolitan area network (MAN), a wide area network (WAN), a broadband network (BBN), the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computing system 800 includes servers and personal computer devices. A personal computing device and server are generally remote from each other and typically interact through a communication network. The relationship of client and server arises by virtue of computer programs running on the respective computers and having a client-server relationship to each other. Computer system 800 can be, for example, and without limitation, a desktop computer, laptop computer, or tablet computer. Computer system 800 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer readable medium" as used herein refers to any medium or media that participates in providing instructions or data to processor 802 for execution. Such a medium may take many forms, including, but not limited to, non-volatile media, volatile media, and transmission media. Non-volatile media include, for example, optical disks, magnetic disks, or flash memory, such as data storage device 806. Volatile media include dynamic memory, such as memory 804. Transmission media include coaxial cables, copper wire, and fiber optics, including the wires that comprise bus 808. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

In one aspect, a method may be an operation, an instruction, or a function and vice versa. In one aspect, a clause or a claim may be amended to include some or all of the words (e.g., instructions, operations, functions, or components) recited in other one or more clauses, one or more words, one or more sentences, one or more phrases, one or more paragraphs, and/or one or more claims.

To illustrate the interchangeability of hardware and software, items, such as the various illustrative blocks, modules, components, methods, operations, instructions, and algorithms, have been described generally in terms of their functionality. Whether such functionality is implemented as hardware, software or a combination of hardware and software depends upon the particular application and design constraints imposed on the overall system. Skilled artisans may implement the described functionality in varying ways for each particular application.

As used herein, the phrase "at least one of" preceding a series of items, with the terms "and" or "or" to separate any of the items, modifies the list as a whole, rather than each member of the list (e.g., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

In one aspect, a term field effect transistor (FET) may refer to any of a variety of multi-terminal transistors generally operating on the principals of controlling an electric field to control the shape and hence the conductivity of a channel of one type of charge carrier in a semiconductor material, including, but not limited to a metal oxide semiconductor field effect transistor (MOSFET), a junction FET (FET), a metal semiconductor FET (MESFET), a high electron mobility transistor (HEMT), a modulation doped FET (MODFET), an insulated gate bipolar transistor (IGBT), a fast reverse epitaxial diode FET (FREDFET), and an ion-sensitive FET (ISFET).

To the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments. Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description. No claim element is to be construed under the provisions of 35 U.S.C. § 112, sixth paragraph, unless the element is expressly recited using the phrase "means for" or, in the case of a method claim, the element is recited using the phrase "step for."

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

What is claimed is:

1. An infusion pump configured for detection of a fluid condition in a flexible tube, the infusion pump comprising:
   a restraining element for receiving the tube;
   a sensor coupled to the restraining element and positioned to obtain a value of a tubing force when the tube is engaged by the restraining element;
   a memory storing instructions; and
   a processor configured to execute the instructions to:
   generate a force-time curve representative of values of the tubing force obtained by the sensor over time;
   determine a time-decaying parameter associated with the tubing force characterizing the force-time curve;
   determine a fluid pressure value for a fluid in the tube based at least in part on the time-decaying parameter;
   introduce a pump reversal event; and
   detect that a rate of change of the tubing force exceeds a threshold.

2. The infusion pump of claim 1, further comprising generating an alarm, wherein the alarm indicates a soft upstream occlusion event based on a rate of change of a stress relaxation value of the tube.

3. The infusion pump of claim 1, further comprising generating an alarm, wherein the alarm indicates a hard upstream occlusion event based on a difference between a measured total force from the tube and an expected force from the tube.

4. The infusion pump of claim 1, wherein the processor is configured to:
   detect an anomaly in at least one of the fluid pressure value or the time-decaying parameter; and
   activate an alarm based on the detected anomaly.

5. The infusion pump of claim 4, wherein to activate the alarm, the processor is further configured to compare the parameters for fitting the force-time curve with a selected threshold.

6. The infusion pump of claim 4, wherein the force-time curve is a first force-time curve, wherein the value of the tubing force is collected over a first period of time, and to activate the alarm, the processor is further configured to compare the parameters for fitting the first force-time curve to a parameter for fitting a second force-time curve, the second force-time curve comprising values of the tubing force collected over a second period of time longer than the first period of time.

7. The infusion pump of claim 4, wherein to activate the alarm, the processor is further configured to compare the parameters for fitting the force-time curve with a history of stored parameters for fitting stored force-time curves with past collected values of the tubing force.

8. The infusion pump of claim 1, wherein the value of the tubing force comprises one of multiple force values obtained over any interval of time during which the tube and sensor are coupled.

9. The infusion pump of claim 1, wherein to determine the fluid pressure value, the processor is further configured to scale a force difference using a relation between a change in fluid force and a corresponding change in total tube-wall force.

10. The infusion pump of claim 1, wherein to identify an occlusion condition the processor is further configured to identify one of a full blockage and a partial blockage of a fluid flow path through the tube.

11. The infusion pump of claim 1, further comprising an analog to digital converter coupling the sensor with the processor to provide a digital representation of the value of the tubing force.

12. A method, comprising:
   generating, with a fluid displacement infusion pump, a fluid flow in a tube;
   deforming the tube with a restraining element coupled with a wall of the tube;
   collecting, with a force sensor comprising the restraining element, a value of a tubing force in response to a wall deformation caused by deforming the tube;
   determining, with a processor, parameters for fitting a curve, the curve comprising values of the tubing force obtained by the force sensor over time, wherein the parameters for fitting the curve comprise at least one time-decaying parameter associated with the tubing force;

determining a fluid pressure value for a fluid in the tube based on the parameters for fitting the curve;

generating, in the fluid displacement infusion pump, a transient reversal of the fluid flow in the tube;

determining a change in the tubing force from a baseline force responsive to the transient reversal; and identifying a blockage condition in the tube based on the change in the tubing force.

13. The method of claim 12, further comprising activating an alarm when the blockage condition in the tube is identified, wherein the alarm indicates one of:

a soft upstream occlusion event based on a rate of change of a stress relaxation value of the tube; and a hard upstream occlusion event based on a difference between a measured total force from the tube and an expected force from the tube.

14. The method of claim 12, further comprising:

identifying an occlusion condition in the tube based on one of the fluid pressure value and the parameters for fitting the curve; and activating an alarm when the occlusion condition is identified in the tube.

15. The method of claim 14, wherein activating the alarm comprises comparing the parameters for fitting the curve with a selected threshold.

16. The method of claim 14, wherein the curve is a first curve, wherein the value of the tubing force is collected over a first period of time and activating the alarm comprises comparing the parameters for fitting the first curve to a parameter for fitting a second curve, the second curve comprising values of the tubing force collected over a second period of time longer than the first period of time.

17. The method of claim 14, wherein activating the alarm comprises comparing the parameters for fitting the curve with a history of stored parameters for fitting stored curves with past collected values of the tubing force.

18. The method of claim 14, wherein identifying an occlusion condition comprises identifying one of a full blockage and a partial blockage of a fluid flow path through the tube.

19. The method of claim 12, wherein determining the fluid pressure value comprises one of:

determining a difference between the value of the tubing force and a model-estimation of the tubing force; and scaling a force difference using a relation between a change in fluid force and a corresponding change in total tube-wall force.

20. The method of claim 12, further comprising providing a digital representation of the value of the tubing force with an analog to digital converter coupling the force sensor with the processor.

* * * * *